United States Patent
Caianiello et al.

(10) Patent No.: US 12,234,256 B2
(45) Date of Patent: Feb. 25, 2025

(54) MOLECULAR DEGRADERS OF EXTRACELLULAR PROTEINS

(71) Applicant: YALE UNIVERSITY, New Haven, CT (US)

(72) Inventors: David Caianiello, New Haven, CT (US); Edward DeRamon, New Haven, CT (US); David Spiegel, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 18/180,634

(22) Filed: Mar. 8, 2023

(65) Prior Publication Data

US 2023/0271994 A1  Aug. 31, 2023

Related U.S. Application Data

(63) Continuation of application No. PCT/US2022/075527, filed on Aug. 26, 2022.

(60) Provisional application No. 63/237,627, filed on Aug. 27, 2021.

(51) Int. Cl.
| C07H 15/18 | (2006.01) |
| A61P 9/00 | (2006.01) |
| C07D 225/08 | (2006.01) |

(52) U.S. Cl.
CPC ............... C07H 15/18 (2013.01); A61P 9/00 (2018.01); C07D 225/08 (2013.01)

(58) Field of Classification Search
CPC .......... C07H 15/18; A61P 9/00; C07D 225/08
USPC ....................................... 536/17.2
See application file for complete search history.

(56) References Cited

U.S. PATENT DOCUMENTS

| 2010/0209445 A1 | 8/2010 | Jahns et al. |
| 2014/0273015 A1* | 9/2014 | Holthoff ............ G01N 33/6893 435/69.6 |
| 2016/0207953 A1 | 7/2016 | Liras et al. |
| 2021/0139436 A1 | 5/2021 | Spiegel et al. |

FOREIGN PATENT DOCUMENTS

| WO | 2010086337 A1 | 8/2010 |
| WO | 2019199621 A1 | 10/2019 |
| WO | 2020237078 A1 | 11/2020 |
| WO | 2021072269 A1 | 4/2021 |
| WO | WO 2021/072246 * | 4/2021 |
| WO | 2021133644 A1 | 7/2021 |
| WO | 2021142377 A2 | 7/2021 |
| WO | 2021155317 A1 | 8/2021 |
| WO | 2022157626 A1 | 7/2022 |

OTHER PUBLICATIONS

Glossary of medical education terms, Institute of International Medical Education. http://www.iime.org/glossary.htm Accessed in Mar. 2013. (Year: 2013).*
Kawai et al. ß1 Adrenergic Receptor Autoantibodies and IgG Subclasses: Current Status and Unsolved Issues. J. Cardiovasc. Dev. Dis. 10, 390, 2023 (15 pages). (Year: 2023).*
Mamidyala et al. Glycomimetic Ligands for the Human Asialoglycoprotein Receptor. J. Am. Chem. Soc. 134, 1978-1981, 2012 (including Supporting information, p. S1 to S26) (Year: 2012).*
International Search Report and Written Opinion for International Application No. PCT/US2022/075535 dated Nov. 21, 2022.
Search results Oct. 3, 2023, Query: US-18-180-686-1 (SEQ ID No. 1) (Year: 2023).
International Search Report and Written Opinion for International Application No. PCT/US2022/075527 dated Dec. 7, 2022.

* cited by examiner

*Primary Examiner* — Yih-Horng Shiao
(74) *Attorney, Agent, or Firm* — Saul Ewing LLP; Kathryn Doyle; Domingos J. Silva

(57) ABSTRACT

The disclosure describes compounds of Formula Ia, which in non-limiting aspects contain an asialoglycoprotein receptor (ASGPR) binding moiety and an anti-$\beta_1$AR binding moiety. Compounds of Formula Ia are useful in preventing, treating, and/or ameliorating heart failure in a subject when administered in therapeutically effective amounts.

14 Claims, 9 Drawing Sheets

Specification includes a Sequence Listing.

A
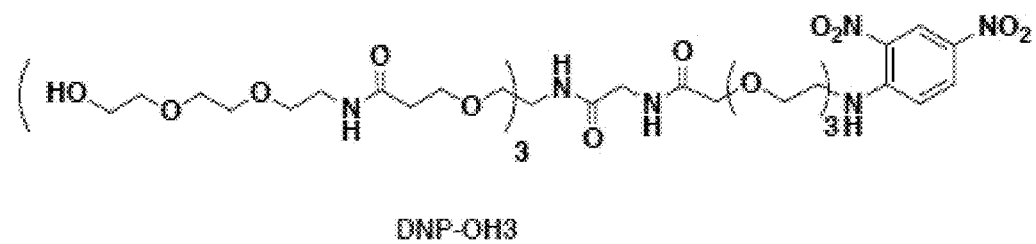
DNP-OH3
FIG. 5
FIG. 6A
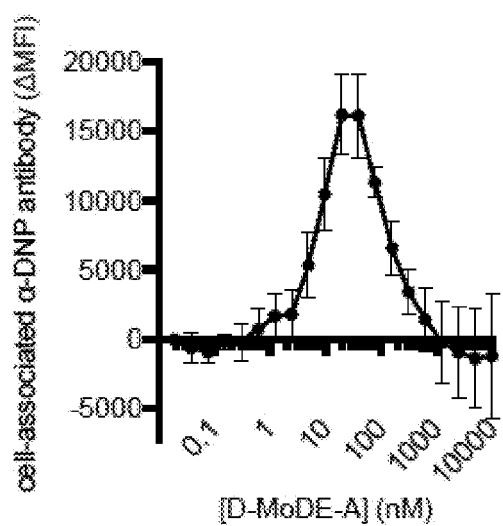
FIG. 6B
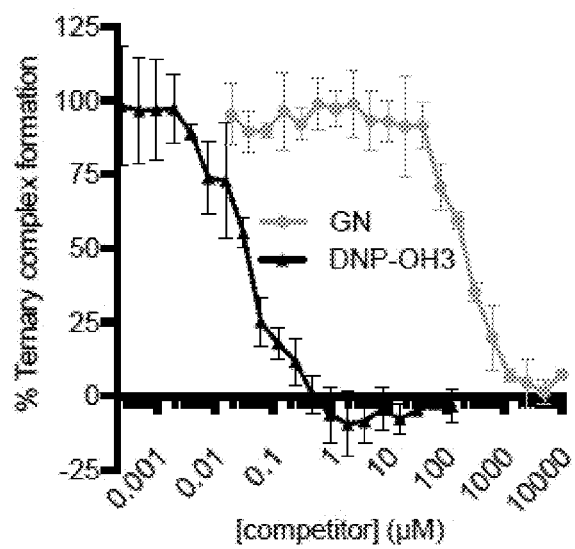
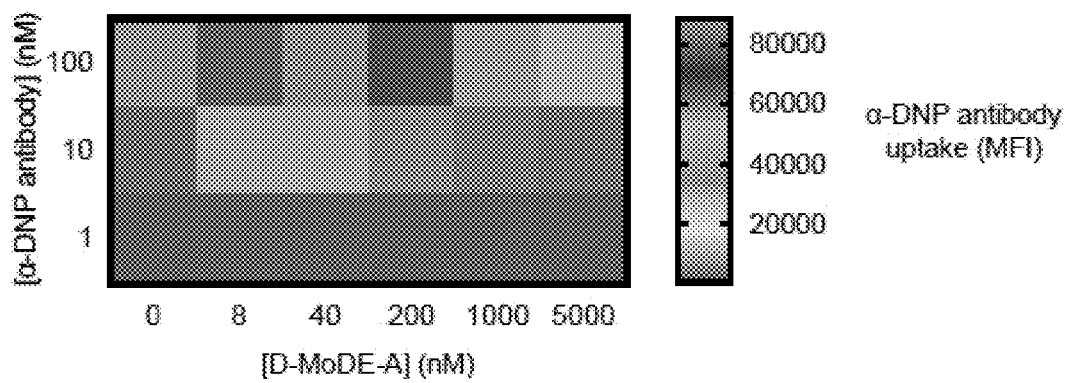
FIG. 6C FIG. 7A
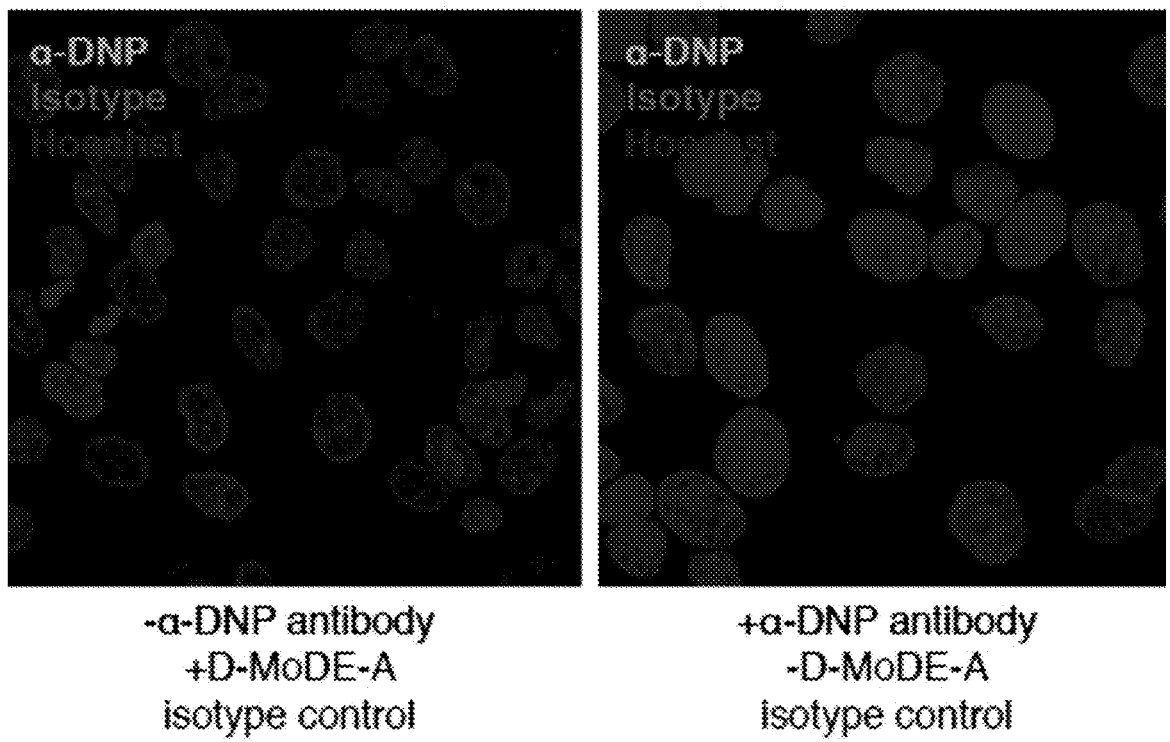
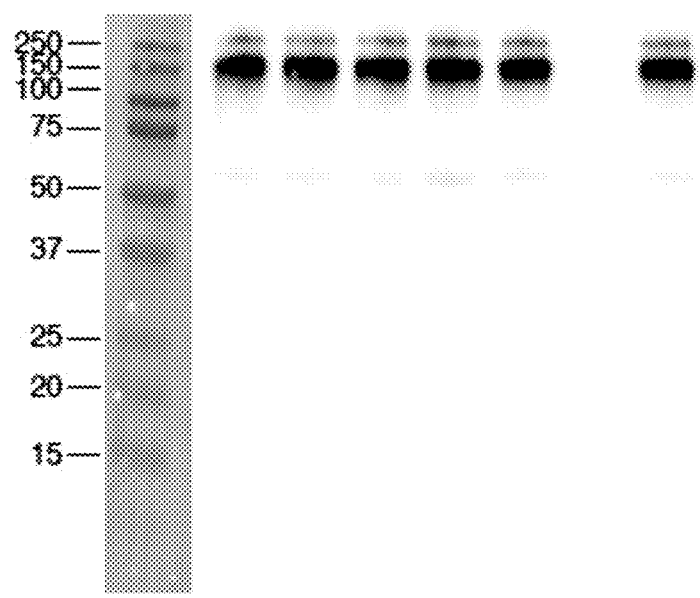
FIG. 7B FIG. 8A
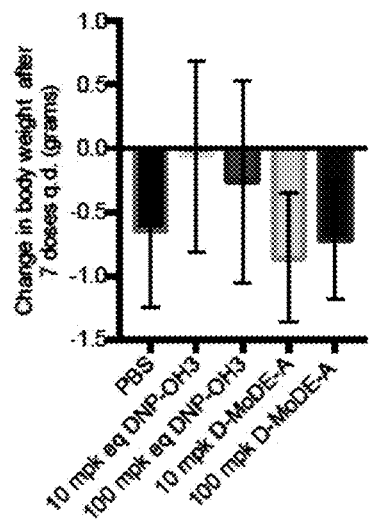
FIG. 8B
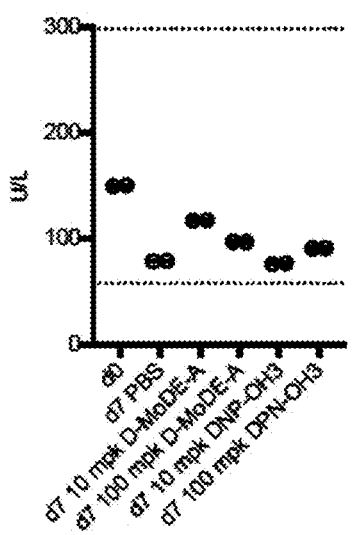
FIG. 8C
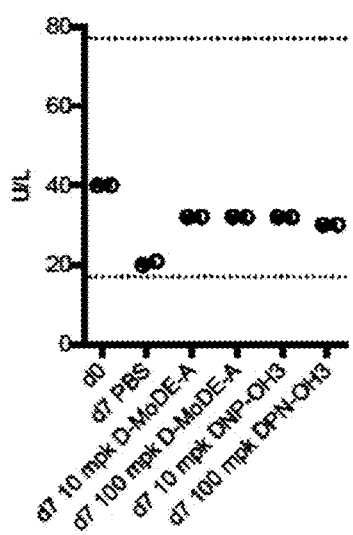
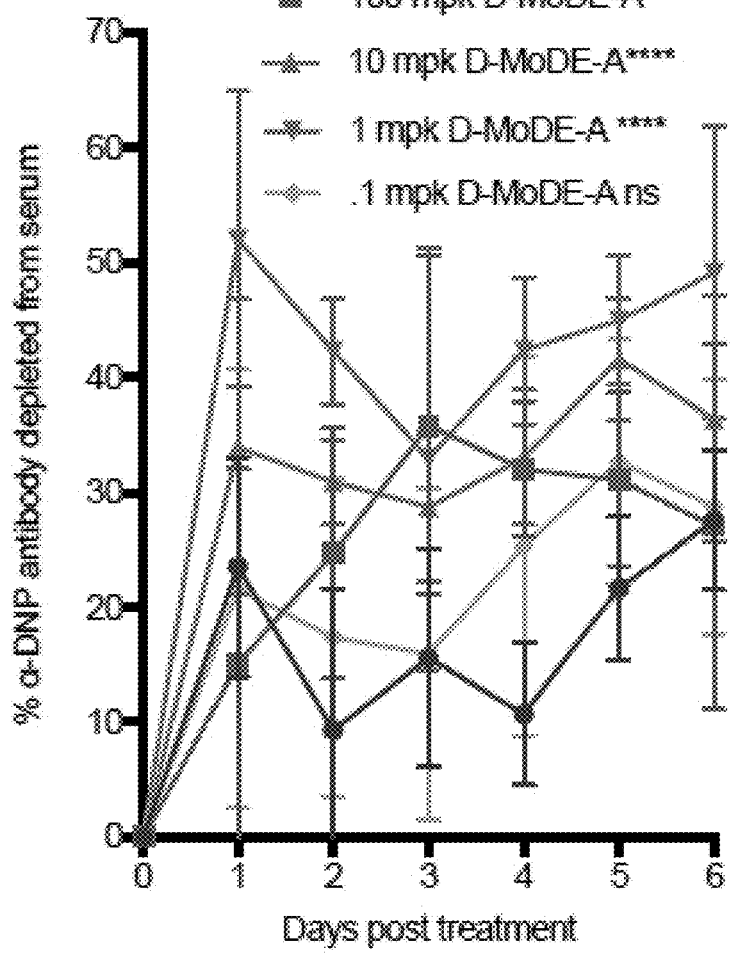
FIG. 8D

```
                         SEQUENCE LISTING

Sequence total quantity: 68
SEQ ID NO: 1            moltype = AA  length = 17
FEATURE                 Location/Qualifiers
REGION                  1..17
                        note = Chemically Synthesized
source                  1..17
                        mol_type = protein
                        organism = synthetic construct
SEQUENCE: 1
DEARRCYNDP KCSDFVQ                                                    17

SEQ ID NO: 2            moltype = AA  length = 17
FEATURE                 Location/Qualifiers
REGION                  1..17
                        note = Chemically Synthesized
SITE                    1
                        note = misc_feature - N-acetylated
SITE                    11
                        note = misc_feature - Xaa = neorleucine
SITE                    17
                        note = misc_feature - terminus is C(=O)NH2
source                  1..17
                        mol_type = protein
                        organism = synthetic construct
SEQUENCE: 2
VKFNKPFVFL XIEQNTK                                                    17

SEQ ID NO: 3            moltype = AA  length = 17
FEATURE                 Location/Qualifiers
REGION                  1..17
                        note = Chemically Synthesized
source                  1..17
                        mol_type = protein
                        organism = synthetic construct
SEQUENCE: 3
VKFNKPFVFL MIEQNTK                                                    17

SEQ ID NO: 4            moltype = AA  length = 20
FEATURE                 Location/Qualifiers
REGION                  1..20
                        note = Chemically Synthesized
source                  1..20
                        mol_type = protein
                        organism = synthetic construct
SEQUENCE: 4
TWPKHFDKHT FYSILKLGKH                                                 20

SEQ ID NO: 5            moltype = AA  length = 19
FEATURE                 Location/Qualifiers
REGION                  1..19
                        note = Chemically Synthesized
source                  1..19
                        mol_type = protein
                        organism = synthetic construct
SEQUENCE: 5
TFFYGGSRGK RNNFKTEEY                                                  19

SEQ ID NO: 6            moltype = AA  length = 30
FEATURE                 Location/Qualifiers
REGION                  1..30
                        note = Chemically Synthesized
```

```
source                  1..30
                        mol_type = protein
                        organism = synthetic construct
SEQUENCE: 6
LRKLRKRLLR DADDLLRKLR KRLLRDADDL                                           30

SEQ ID NO: 7            moltype = AA  length = 20
FEATURE                 Location/Qualifiers
REGION                  1..20
                        note = Chemically Synthesized
source                  1..20
                        mol_type = protein
                        organism = synthetic construct
SEQUENCE: 7
TEELRVRLAS HLRKLRKRLL                                                      20

SEQ ID NO: 8            moltype = AA  length = 22
FEATURE                 Location/Qualifiers
REGION                  1..22
                        note = Chemically Synthesized
source                  1..22
                        mol_type = protein
                        organism = synthetic construct
SEQUENCE: 8
EAKIEKHNHY QKQLEIAHEK LR                                                   22

SEQ ID NO: 9            moltype = AA  length = 19
FEATURE                 Location/Qualifiers
REGION                  1..19
                        note = Chemically Synthesized
source                  1..19
                        mol_type = protein
                        organism = synthetic construct
SEQUENCE: 9
TFFYGGSRGK RNNFKTEEY                                                       19

SEQ ID NO: 10           moltype = AA  length = 8
FEATURE                 Location/Qualifiers
REGION                  1..8
                        note = Chemically Synthesized
SITE                    1
                        note = misc_feature - Cys is a D-amino acid
REGION                  1..8
                        note = misc_feature - Cys and Pen form a ring
SITE                    3
                        note = misc_feature - Xaa = thiazolidine-4-carboxylic acid
SITE                    8
                        note = misc_feature - Xaa = Penicillamine
source                  1..8
                        mol_type = protein
                        organism = synthetic construct
SEQUENCE: 10
CMXRLRGX                                                                    8

SEQ ID NO: 11           moltype = AA  length = 8
FEATURE                 Location/Qualifiers
REGION                  1..8
                        note = Chemically Synthesized
REGION                  1..8
                        note = misc_feature - Cys and Cys form a ring
source                  1..8
                        mol_type = protein
                        organism = synthetic construct
SEQUENCE: 11
CMPRLRGC                                                                    8

SEQ ID NO: 12           moltype = AA  length = 12
FEATURE                 Location/Qualifiers
REGION                  1..12
                        note = Chemically Synthesized
REGION                  4..9
                        note = misc_feature - Cys and Cys form a ring
source                  1..12
                        mol_type = protein
                        organism = synthetic construct
SEQUENCE: 12
HLDCMPRGCF RN                                                              12
```

```
SEQ ID NO: 13              moltype = AA   length = 9
FEATURE                    Location/Qualifiers
REGION                     1..9
                           note = Chemically Synthesized
REGION                     1..9
                           note = misc_feature - Cys and Cys form a ring
source                     1..9
                           mol_type = protein
                           organism = synthetic construct
SEQUENCE: 13
CQVKSMPRC                                                                  9

SEQ ID NO: 14              moltype = AA   length = 9
FEATURE                    Location/Qualifiers
REGION                     1..9
                           note = Chemically Synthesized
REGION                     1..9
                           note = misc_feature - Cys and Cys form a ring
source                     1..9
                           mol_type = protein
                           organism = synthetic construct
SEQUENCE: 14
CTTPMPRLC                                                                  9

SEQ ID NO: 15              moltype = AA   length = 9
FEATURE                    Location/Qualifiers
REGION                     1..9
                           note = Chemically Synthesized
REGION                     1..9
                           note = misc_feature - Cys and Cys form a ring
source                     1..9
                           mol_type = protein
                           organism = synthetic construct
SEQUENCE: 15
CKAPQMPRC                                                                  9

SEQ ID NO: 16              moltype = AA   length = 9
FEATURE                    Location/Qualifiers
REGION                     1..9
                           note = Chemically Synthesized
REGION                     1..9
                           note = misc_feature - Cys and Cys form a ring
source                     1..9
                           mol_type = protein
                           organism = synthetic construct
SEQUENCE: 16
CLNPSMPRC                                                                  9

SEQ ID NO: 17              moltype = AA   length = 9
FEATURE                    Location/Qualifiers
REGION                     1..9
                           note = Chemically Synthesized
source                     1..9
                           mol_type = protein
                           organism = synthetic construct
SEQUENCE: 17
CLVSSMPRC                                                                  9

SEQ ID NO: 18              moltype = AA   length = 9
FEATURE                    Location/Qualifiers
REGION                     1..9
                           note = Chemically Synthesized
REGION                     1..9
                           note = misc_feature - Cys and Cys form a ring
source                     1..9
                           mol_type = protein
                           organism = synthetic construct
SEQUENCE: 18
CLQPMPRLC                                                                  9

SEQ ID NO: 19              moltype = AA   length = 9
FEATURE                    Location/Qualifiers
REGION                     1..9
                           note = Chemically Synthesized
REGION                     1..9
                           note = misc_feature - Cys and Cys form a ring
```

```
source                    1..9
                          mol_type = protein
                          organism = synthetic construct
SEQUENCE: 19
CPVSSMPRC                                                                    9

SEQ ID NO: 20             moltype = AA  length = 9
FEATURE                   Location/Qualifiers
REGION                    1..9
                          note = Chemically Synthesized
REGION                    1..9
                          note = misc_feature - Cys and Cys form a ring
source                    1..9
                          mol_type = protein
                          organism = synthetic construct
SEQUENCE: 20
CQSPMPRLC                                                                    9

SEQ ID NO: 21             moltype = AA  length = 9
FEATURE                   Location/Qualifiers
REGION                    1..9
                          note = Chemically Synthesized
REGION                    1..9
                          note = misc_feature - Cys and Cys form a ring
source                    1..9
                          mol_type = protein
                          organism = synthetic construct
SEQUENCE: 21
CLTPMPRLC                                                                    9

SEQ ID NO: 22             moltype = AA  length = 15
FEATURE                   Location/Qualifiers
REGION                    1..15
                          note = Chemically Synthesized
REGION                    5..12
                          note = misc_feature - Cys and Cys form a ring
source                    1..15
                          mol_type = protein
                          organism = synthetic construct
SEQUENCE: 22
DSGLCMPRLR GCDPR                                                            15

SEQ ID NO: 23             moltype = AA  length = 15
FEATURE                   Location/Qualifiers
REGION                    1..15
                          note = Chemically Synthesized
source                    1..15
                          mol_type = protein
                          organism = synthetic construct
SEQUENCE: 23
TPSAHAMALQ SLSVG                                                            15

SEQ ID NO: 24             moltype = AA  length = 15
FEATURE                   Location/Qualifiers
REGION                    1..15
                          note = Chemically Synthesized
SITE                      1
                          note = misc_feature - N-acetylated
REGION                    5..12
                          note = misc_feature - Cys and Cys form a ring
SITE                      15
                          note = misc_feature - terminus is C(=O)NH2
source                    1..15
                          mol_type = protein
                          organism = synthetic construct
SEQUENCE: 24
DSGLCMPRLR GCDPR                                                            15

SEQ ID NO: 25             moltype = AA  length = 8
FEATURE                   Location/Qualifiers
REGION                    1..8
                          note = Chemically Synthesized
REGION                    1..8
                          note = misc_feature - Cys and Cys form a ring
SITE                      1
                          note = misc_feature - N-propionylated
SITE                      8
                          note = misc_feature - terminus is (C=O)NH2
```

```
source                    1..8
                          mol_type = protein
                          organism = synthetic construct
SEQUENCE: 25
CMPRLRGC                                                                     8

SEQ ID NO: 26             moltype = AA   length = 8
FEATURE                   Location/Qualifiers
REGION                    1..8
                          note = Chemically Synthesized
REGION                    1..8
                          note = misc_feature - Cys and Cys form a ring
SITE                      1
                          note = misc_feature - N-propionylated D-amino acid
SITE                      8
                          note = misc_feature - terminus is C(=O)NH2
source                    1..8
                          mol_type = protein
                          organism = synthetic construct
SEQUENCE: 26
CMPRLRGC                                                                     8

SEQ ID NO: 27             moltype = AA   length = 8
FEATURE                   Location/Qualifiers
REGION                    1..8
                          note = Chemically Synthesized
SITE                      1
                          note = misc_feature - Propionylated D-amino acid
REGION                    1..8
                          note = misc_feature - Cys and Pen form a ring
SITE                      3
                          note = misc_feature - Xaa = thiazolidine-4-carboxylic acid
SITE                      8
                          note = misc_feature - Xaa = penacillamine, terminus is
                           C(=O)NH2
source                    1..8
                          mol_type = protein
                          organism = synthetic construct
SEQUENCE: 27
CMXRLRGX                                                                     8

SEQ ID NO: 28             moltype = AA   length = 7
FEATURE                   Location/Qualifiers
REGION                    1..7
                          note = Chemically Synthesized
REGION                    1..7
                          note = misc_feature - Cys and Cys form a ring
SITE                      1
                          note = misc_feature - N-acetylated
SITE                      7
                          note = misc_feature - terminus is C(=O)NH2
source                    1..7
                          mol_type = protein
                          organism = synthetic construct
SEQUENCE: 28
CMPRLGC                                                                      7

SEQ ID NO: 29             moltype = AA   length = 8
FEATURE                   Location/Qualifiers
REGION                    1..8
                          note = Chemically Synthesized
REGION                    1..8
                          note = misc_feature - Cys and Cys form a ring
SITE                      1
                          note = misc_feature - N-acetylated D-amino acid
SITE                      8
                          note = misc_feature - terminus is C(=O)NH2
source                    1..8
                          mol_type = protein
                          organism = synthetic construct
SEQUENCE: 29
CMPRLRGC                                                                     8

SEQ ID NO: 30             moltype = AA   length = 9
FEATURE                   Location/Qualifiers
REGION                    1..9
                          note = Chemically Synthesized
SITE                      1
                          note = misc_feature - N-acetylated
```

```
REGION                  2..9
                        note = misc_feature - Pen and Cys form a ring
SITE                    2
                        note = misc_feature - Xaa = Penicillamine
SITE                    4
                        note = misc_feature - Xaa = thiazolidine-4-carboxylic acid
SITE                    9
                        note = misc_feature - terminus is C(=O)NH2
source                  1..9
                        mol_type = protein
                        organism = synthetic construct
SEQUENCE: 30
DXMXRLRGC                                                                         9

SEQ ID NO: 31           moltype = AA  length = 8
FEATURE                 Location/Qualifiers
REGION                  1..8
                        note = Chemically Synthesized
SITE                    1
                        note = misc_feature - N-propionylated D-amino acid
REGION                  1..8
                        note = misc_feature - Cys and Pen form a ring
SITE                    3
                        note = misc_feature - Xaa = thiazolidine-4-carboxylic acid
SITE                    8
                        note = misc_feature - Xaa = Penicillamine, terminus is
                         C(=O)NH2
source                  1..8
                        mol_type = protein
                        organism = synthetic construct
SEQUENCE: 31
CMXRLRGX                                                                          8

SEQ ID NO: 32           moltype = AA  length = 8
FEATURE                 Location/Qualifiers
REGION                  1..8
                        note = Chemically Synthesized
SITE                    1
                        note = misc_feature - N-propionylated
REGION                  1..8
                        note = misc_feature - Cys and Pen form a ring
SITE                    3
                        note = misc_feature - Xaa = thiazolidine-4-carboxylic acid
SITE                    7
                        note = misc_feature - Xaa = Sarcosine
SITE                    8
                        note = misc_feature - Xaa = Penicillamine, terminus is
                         C(=O)NH2
source                  1..8
                        mol_type = protein
                        organism = synthetic construct
SEQUENCE: 32
CMXRLRXX                                                                          8

SEQ ID NO: 33           moltype = AA  length = 8
FEATURE                 Location/Qualifiers
REGION                  1..8
                        note = Chemically Synthesized
SITE                    1
                        note = misc_feature - N-propionylated D-amino acid
REGION                  1..8
                        note = misc_feature - Cys and Cys form ring
SITE                    3
                        note = misc_feature - Xaa = Pipecolic group
SITE                    7
                        note = misc_feature - Xaa = Sarcosine
SITE                    8
                        note = misc_feature - terminus is C(=O)NH2
source                  1..8
                        mol_type = protein
                        organism = synthetic construct
SEQUENCE: 33
CMXRLRXC                                                                          8

SEQ ID NO: 34           moltype = AA  length = 8
FEATURE                 Location/Qualifiers
REGION                  1..8
                        note = Chemically Synthesized
```

```
SITE                      1
                          note = misc_feature - N-propionylated D-amino acid
REGION                    1..8
                          note = misc_feature - Cys and Pen form a ring
SITE                      3
                          note = misc_feature - Xaa = Pipecolic group
SITE                      8
                          note = misc_feature - Xaa = penacillamine, terminus is
                           C(=O)NH2
source                    1..8
                          mol_type = protein
                          organism = synthetic construct
SEQUENCE: 34
CMXRLRGX                                                                      8

SEQ ID NO: 35             moltype = AA  length = 8
FEATURE                   Location/Qualifiers
REGION                    1..8
                          note = Chemically Synthesized
SITE                      1
                          note = misc_feature - N-propionylated D-amino acid
REGION                    1..8
                          note = misc_feature - Cys and Pen form a ring
SITE                      3
                          note = misc_feature - Xaa = Pipecolic group
SITE                      7
                          note = misc_feature - Xaa = Sarcosine
SITE                      8
                          note = misc_feature - Xaa = penacillamine, terminus is
                           C(=O)NH2
source                    1..8
                          mol_type = protein
                          organism = synthetic construct
SEQUENCE: 35
CMXRLRXX                                                                      8

SEQ ID NO: 36             moltype = AA  length = 16
FEATURE                   Location/Qualifiers
REGION                    1..16
                          note = Chemically Synthesized
REGION                    4..13
                          note = misc_feature - Cys and Cys form a ring
source                    1..16
                          mol_type = protein
                          organism = synthetic construct
SEQUENCE: 36
TDTCLMLPLL LGCDEE                                                             16

SEQ ID NO: 37             moltype = AA  length = 16
FEATURE                   Location/Qualifiers
REGION                    1..16
                          note = Chemically Synthesized
REGION                    4..13
                          note = misc_feature - Cys and Cys form a ring
source                    1..16
                          mol_type = protein
                          organism = synthetic construct
SEQUENCE: 37
DPICWYFPRL LGCTTL                                                             16

SEQ ID NO: 38             moltype = AA  length = 16
FEATURE                   Location/Qualifiers
REGION                    1..16
                          note = Chemically Synthesized
REGION                    4..13
                          note = misc_feature - Cys and Cys form a ring
source                    1..16
                          mol_type = protein
                          organism = synthetic construct
SEQUENCE: 38
WYPCYIYPRL LGCDGD                                                             16

SEQ ID NO: 39             moltype = AA  length = 16
FEATURE                   Location/Qualifiers
REGION                    1..16
                          note = Chemically Synthesized
REGION                    4..13
                          note = misc_feature - Cys and Cys form a ring
```

```
source                  1..16
                        mol_type = protein
                        organism = synthetic construct
SEQUENCE: 39
GNICMLIPGL LGCSYE                                                16

SEQ ID NO: 40           moltype = AA  length = 16
FEATURE                 Location/Qualifiers
REGION                  1..16
                        note = Chemically Synthesized
REGION                  4..13
                        note = misc_feature - Cys and Cys form a ring
source                  1..16
                        mol_type = protein
                        organism = synthetic construct
SEQUENCE: 40
VNSCLLLPNL LGCGDD                                                16

SEQ ID NO: 41           moltype = AA  length = 16
FEATURE                 Location/Qualifiers
REGION                  1..16
                        note = Chemically Synthesized
REGION                  4..13
                        note = misc_feature - Cys and Cys form a ring
source                  1..16
                        mol_type = protein
                        organism = synthetic construct
SEQUENCE: 41
TPVCILLPSL LGCDTQ                                                16

SEQ ID NO: 42           moltype = AA  length = 16
FEATURE                 Location/Qualifiers
REGION                  1..16
                        note = Chemically Synthesized
REGION                  4..13
                        note = misc_feature - Cys and Cys form a ring
source                  1..16
                        mol_type = protein
                        organism = synthetic construct
SEQUENCE: 42
TVLCSLWPEL LGCPPE                                                16

SEQ ID NO: 43           moltype = AA  length = 16
FEATURE                 Location/Qualifiers
REGION                  1..16
                        note = Chemically Synthesized
REGION                  4..13
                        note = misc_feature - Cys and Cys form a ring
source                  1..16
                        mol_type = protein
                        organism = synthetic construct
SEQUENCE: 43
TFSCLMWPWL LGCESL                                                16

SEQ ID NO: 44           moltype = AA  length = 16
FEATURE                 Location/Qualifiers
REGION                  1..16
                        note = Chemically Synthesized
REGION                  4..13
                        note = misc_feature - Cys and Cys form a ring
source                  1..16
                        mol_type = protein
                        organism = synthetic construct
SEQUENCE: 44
FGTCYTWPWL LGCEGF                                                16

SEQ ID NO: 45           moltype = AA  length = 16
FEATURE                 Location/Qualifiers
REGION                  1..16
                        note = Chemically Synthesized
REGION                  4..13
                        note = misc_feature - Cys and Cys form a ring
source                  1..16
                        mol_type = protein
                        organism = synthetic construct
SEQUENCE: 45
SLFCRLLLTP VGCVSQ                                                16

SEQ ID NO: 46           moltype = AA  length = 16
```

```
FEATURE                 Location/Qualifiers
REGION                  1..16
                        note = Chemically Synthesized
source                  1..16
                        mol_type = protein
                        organism = synthetic construct
SEQUENCE: 46
HLLVLPRGLL GCTTLA                                                   16

SEQ ID NO: 47           moltype = AA   length = 16
FEATURE                 Location/Qualifiers
REGION                  1..16
                        note = Chemically Synthesized
REGION                  4..13
                        note = misc_feature - Cys and Cys form a ring
source                  1..16
                        mol_type = protein
                        organism = synthetic construct
SEQUENCE: 47
TSLCSMFPDL LGCFNL                                                   16

SEQ ID NO: 48           moltype = AA   length = 16
FEATURE                 Location/Qualifiers
REGION                  1..16
                        note = Chemically Synthesized
REGION                  4..13
                        note = misc_feature - Cys and Cys form a ring
source                  1..16
                        mol_type = protein
                        organism = synthetic construct
SEQUENCE: 48
SHPCGRLPML LGCAES                                                   16

SEQ ID NO: 49           moltype = AA   length = 17
FEATURE                 Location/Qualifiers
REGION                  1..17
                        note = Chemically Synthesized
source                  1..17
                        mol_type = protein
                        organism = synthetic construct
SEQUENCE: 49
TSTCSMVPGP LGAVSTW                                                  17

SEQ ID NO: 50           moltype = AA   length = 16
FEATURE                 Location/Qualifiers
REGION                  1..16
                        note = Chemically Synthesized
REGION                  4..13
                        note = misc_feature - Cys and Cys form a ring
source                  1..16
                        mol_type = protein
                        organism = synthetic construct
SEQUENCE: 50
KDPCTRWAML LGCDGE                                                   16

SEQ ID NO: 51           moltype = AA   length = 16
FEATURE                 Location/Qualifiers
REGION                  1..16
                        note = Chemically Synthesized
REGION                  4..13
                        note = misc_feature - Cys and Cys form a ring
source                  1..16
                        mol_type = protein
                        organism = synthetic construct
SEQUENCE: 51
IMTCSVYPFL LGCVDK                                                   16

SEQ ID NO: 52           moltype = AA   length = 16
FEATURE                 Location/Qualifiers
REGION                  1..16
                        note = Chemically Synthesized
REGION                  4..13
                        note = misc_feature - Cys and Cys form a ring
source                  1..16
                        mol_type = protein
                        organism = synthetic construct
SEQUENCE: 52
IHSCAHVMRL LGCWSR                                                   16
```

```
SEQ ID NO: 53            moltype = AA   length = 17
FEATURE                  Location/Qualifiers
REGION                   1..17
                         note = Chemically Synthesized
SITE                     1
                         note = misc_feature - N-acetylated
REGION                   4..14
                         note = misc_feature - Cys and Cys form a ring
SITE                     17
                         note = misc_feature - terminus is C(=O)NH2
source                   1..17
                         mol_type = protein
                         organism = synthetic construct
SEQUENCE: 53
QRFCTGHFGG LYPCNGP                                                          17

SEQ ID NO: 54            moltype = AA   length = 13
FEATURE                  Location/Qualifiers
REGION                   1..13
                         note = Chemically Synthesized
SITE                     1
                         note = misc_feature - N-acetylated
SITE                     3
                         note = misc_feature - Xaa = Penacillamine
REGION                   3..13
                         note = misc_feature - Pen and Cys form a ring
SITE                     9
                         note = misc_feature - Xaa = sarcosine
SITE                     10
                         note = misc_feature - Xaa = N-methylleucine
SITE                     13
                         note = misc_feature - terminus is C(=O)NH2
source                   1..13
                         mol_type = protein
                         organism = synthetic construct
SEQUENCE: 54
RFXTGHFGXX YPC                                                              13

SEQ ID NO: 55            moltype = AA   length = 10
FEATURE                  Location/Qualifiers
REGION                   1..10
                         note = Chemically Synthesized
source                   1..10
                         mol_type = protein
                         organism = synthetic construct
SEQUENCE: 55
CGGGPFWWWP                                                                  10

SEQ ID NO: 56            moltype = AA   length = 10
FEATURE                  Location/Qualifiers
REGION                   1..10
                         note = Chemically Synthesized
source                   1..10
                         mol_type = protein
                         organism = synthetic construct
SEQUENCE: 56
CGGGHKYLRW                                                                  10

SEQ ID NO: 57            moltype = AA   length = 10
FEATURE                  Location/Qualifiers
REGION                   1..10
                         note = Chemically Synthesized
source                   1..10
                         mol_type = protein
                         organism = synthetic construct
SEQUENCE: 57
CGGGKRIFMV                                                                  10

SEQ ID NO: 58            moltype = AA   length = 10
FEATURE                  Location/Qualifiers
REGION                   1..10
                         note = Chemically Synthesized
source                   1..10
                         mol_type = protein
                         organism = synthetic construct
SEQUENCE: 58
CGGGKWHYLR                                                                  10

SEQ ID NO: 59            moltype = AA   length = 12
```

```
FEATURE                 Location/Qualifiers
REGION                  1..12
                        note = Chemically Synthesized
source                  1..12
                        mol_type = protein
                        organism = synthetic construct
SEQUENCE: 59
THRPPMWSPV WP                                                                    12

SEQ ID NO: 60           moltype = AA  length = 7
FEATURE                 Location/Qualifiers
REGION                  1..7
                        note = Chemically Synthesized
source                  1..7
                        mol_type = protein
                        organism = synthetic construct
SEQUENCE: 60
HAIYPRH                                                                           7

SEQ ID NO: 61           moltype = AA  length = 12
FEATURE                 Location/Qualifiers
REGION                  1..12
                        note = Chemically Synthesized
source                  1..12
                        mol_type = protein
                        organism = synthetic construct
SEQUENCE: 61
THRPPMWSPV WP                                                                    12

SEQ ID NO: 62           moltype = AA  length = 12
FEATURE                 Location/Qualifiers
REGION                  1..12
                        note = Chemically Synthesized
source                  1..12
                        mol_type = protein
                        organism = synthetic construct
SEQUENCE: 62
THRPPMWSPV WP                                                                    12

SEQ ID NO: 63           moltype = AA  length = 15
FEATURE                 Location/Qualifiers
REGION                  1..15
                        note = Chemically Synthesized
source                  1..15
                        mol_type = protein
                        organism = synthetic construct
SEQUENCE: 63
LSLERFLRCW SDAPA                                                                 15

SEQ ID NO: 64           moltype = AA  length = 13
FEATURE                 Location/Qualifiers
REGION                  1..13
                        note = Chemically Synthesized
source                  1..13
                        mol_type = protein
                        organism = synthetic construct
SEQUENCE: 64
LERFLRCWSD APA                                                                   13

SEQ ID NO: 65           moltype = AA  length = 11
FEATURE                 Location/Qualifiers
REGION                  1..11
                        note = Chemically Synthesized
source                  1..11
                        mol_type = protein
                        organism = synthetic construct
SEQUENCE: 65
RFLRCWSDAP A                                                                     11

SEQ ID NO: 66           moltype = AA  length = 9
FEATURE                 Location/Qualifiers
REGION                  1..9
                        note = Chemically Synthesized
source                  1..9
                        mol_type = protein
                        organism = synthetic construct
SEQUENCE: 66
LRCWSDAPA                                                                         9
```

```
SEQ ID NO: 67            moltype = AA  length = 7
FEATURE                  Location/Qualifiers
REGION                   1..7
                         note = Chemically Synthesized
source                   1..7
                         mol_type = protein
                         organism = synthetic construct
SEQUENCE: 67
CWSDAPA                                                                        7

SEQ ID NO: 68            moltype = AA  length = 18
FEATURE                  Location/Qualifiers
REGION                   1..18
                         note = Chemically Synthesized
source                   1..18
                         mol_type = protein
                         organism = synthetic construct
SEQUENCE: 68
DWFKAFYDKV AEKFKEAF                                                           18
```

MOLECULAR DEGRADERS OF EXTRACELLULAR PROTEINS

CROSS-REFERENCE TO RELATED APPLICATION

This application is a continuation of, and claims priority to, PCT International Application No. PCT/US2022/075527, filed Aug. 26, 2022, which claims priority to U.S. Provisional Patent Application No. 63/237,627, filed Aug. 27, 2021, the disclosure of each of which is incorporated herein by reference in its entirety.

STATEMENT REGARDING FEDERALLY SPONSORED RESEARCH

This invention was made with government support under GM067543 awarded by National Institutes of Health. The government has certain rights in this invention.

INCORPORATION-BY-REFERENCE OF MATERIAL SUBMITTED AS A TEXT FILE

This disclosure contains one or more sequences in a computer readable format in an accompanying text file titled "047162-7328WO1_ST26.xml," which is 120 KB in size and was generated Aug. 26, 2022, the contents of which are incorporated herein by reference in their entirety.

BACKGROUND

Pathogenic anti-$\beta_1EC_{II}$ (the second extracellular loop of the $\beta_1$ adrenergic receptor) autoantibodies have been shown to cause dilated cardiomyopathy (DCM) and other forms of heart failure. Existing literature has suggested that neutralization or removal of these antibodies can alleviate disease. Existing treatments for DCM, such as $\beta_1$-AR (adrenoreceptor) blockers and whole IgG depletion, are associated with significant undesirable side effects such as fatigue and dizziness, poor circulation, gastrointestinal symptoms, and sexual dysfunction.

Accordingly, there is an ongoing need for more selective and rapidly active treatment of DCM. The present disclosure fulfills this need.

BRIEF SUMMARY

In various aspects, a compound of Formula Ia, or a pharmaceutically acceptable salt thereof is provided.

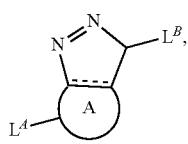

Formula Ia wherein:
  ------ is a carbon-carbon single or double bond;
  A is a $C_{6-18}$ aryl, $C_{6-18}$ heterocyclyl, $C_{6-18}$ biaryl, or $C_{6-18}$ heterobiaryl, each of which is optionally substituted by 1-6 substituents selected from the group consisting of F, Cl, Br, I, ORG, OC(O)N(RG)$_2$, CN, NO, NO$_2$, ONO$_2$, CF$_3$, OCF$_3$, RG, N(RG)$_2$, SRG, SORG, SO$_2$RG, SO$_2$N(RG)$_2$, and SO$_3$RG;

$L^A$ is an ASGPR binding moiety with the structure

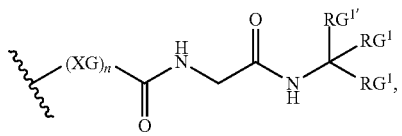

$L^B$ is an anti-$\beta_1$AR binding moiety with the structure

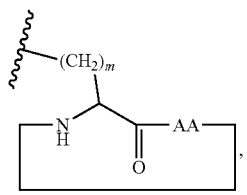

AA is an amino acid sequence at least 80% homologous to SEQ ID NO: 1;
$RG^{1'}$ is

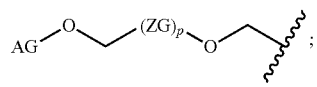

each occurrence of $R^1$ is independently hydrogen or

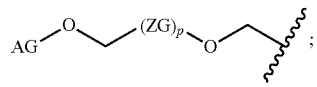

AG is an aminosaccharide;
each occurrence of RG is independently H, optionally substituted $C_{1-10}$ alkyl, optionally substituted $C_{3-10}$ cycloalkyl, optionally substituted $C_{6-18}$ aryl, or optionally substituted $C_{5-18}$ heteroaryl;
each occurrence of XG is independently selected from the group consisting of —CH$_2$—, —C(=O)—, —NH—, and —O—;
each occurrence of ZG is independently selected from the group consisting of —CH$_2$—, —C(=O)—, —NH—, and —O—;
m is an integer from 2 to 10;
n is an integer from 1 to 100; and
p is an integer from 1 to 50.

In various aspects, the compounds of the disclosure are useful in method of preventing, treating, and/or ameliorating heart failure in a subject when administered in therapeutically effective amounts.

BRIEF DESCRIPTION OF THE FIGURES

The drawings illustrate generally, by way of example, but not by way of limitation, various embodiments of the present application.

FIG. 2A shows flow cytometry data showing the successful endocytosis of the target antibody (a$\beta_1$AR) in the presence of varying concentrations compounds of Formula I. FIG. 2B shows inhibition of endocytosis by binding ASGPR or a$\beta_1$AR (anti-B$_1$AR) target antibodies.

FIG. 3A shows flow cytometry data indicating formation of a ternary complex between hepatocytes, compounds of Formula I, and a$\beta_1$AR target antibodies. FIG. 3B shows the fold-change in the concentration of a$\beta_1$AR target antibodies as a function of the dose of compounds of Formula I.

FIG. 5 shows the chemical structure of α-DNP (dinitrophenyl) antibody binding control molecule.

FIGS. 6A-6C show ternary complex formation. FIG. 6A shows formation of a ternary complex between hepatocytes and α-DNP antibody is dependent on the concentration of D-MoDE-A. FIG. 6B shows D-MoDE-A-mediated ternary complex formation is inhibited by competitive binders of either ASGPR or α-DNP antibody. FIG. 6C shows endocytosis of α-DNP antibody in hepatocytes is dependent on both α-DNP antibody and DMoDE-A concentration (12 hour time point).

FIG. 7A shows Alexa 488 signal in colocalization studies is dependent on the presence of α-DNP antibody and D-MoDE-A. Primary antibody is necessary for EEA1/LAMP2 signal. FIG. 7B shows presentative western blot of cell culture supernatants.

FIG. 8A shows mouse body weight following treatment with D-MoDE-A or DNP-OH3. Statistical differences were analyzed by T test. FIG. 8B shows levels of aspartate transaminase (AST) in treated mice. Statistical differences were analyzed by T test. FIG. 8C shows levels of alanine transaminase (ALT) in treated mice. Statistical differences were analyzed by T test. FIG. 8D shows decrease in serum levels of α-DNP antibody following a single variable dose of D-MoDE-A. Each experimental group contained at least eight mice. Statistical differences were assessed by repeated measures two-way ANOVA with Tukey's tests for post-hoc comparison of simple effects between each of the treatment groups and PBS.

DETAILED DESCRIPTION

Figure 1:
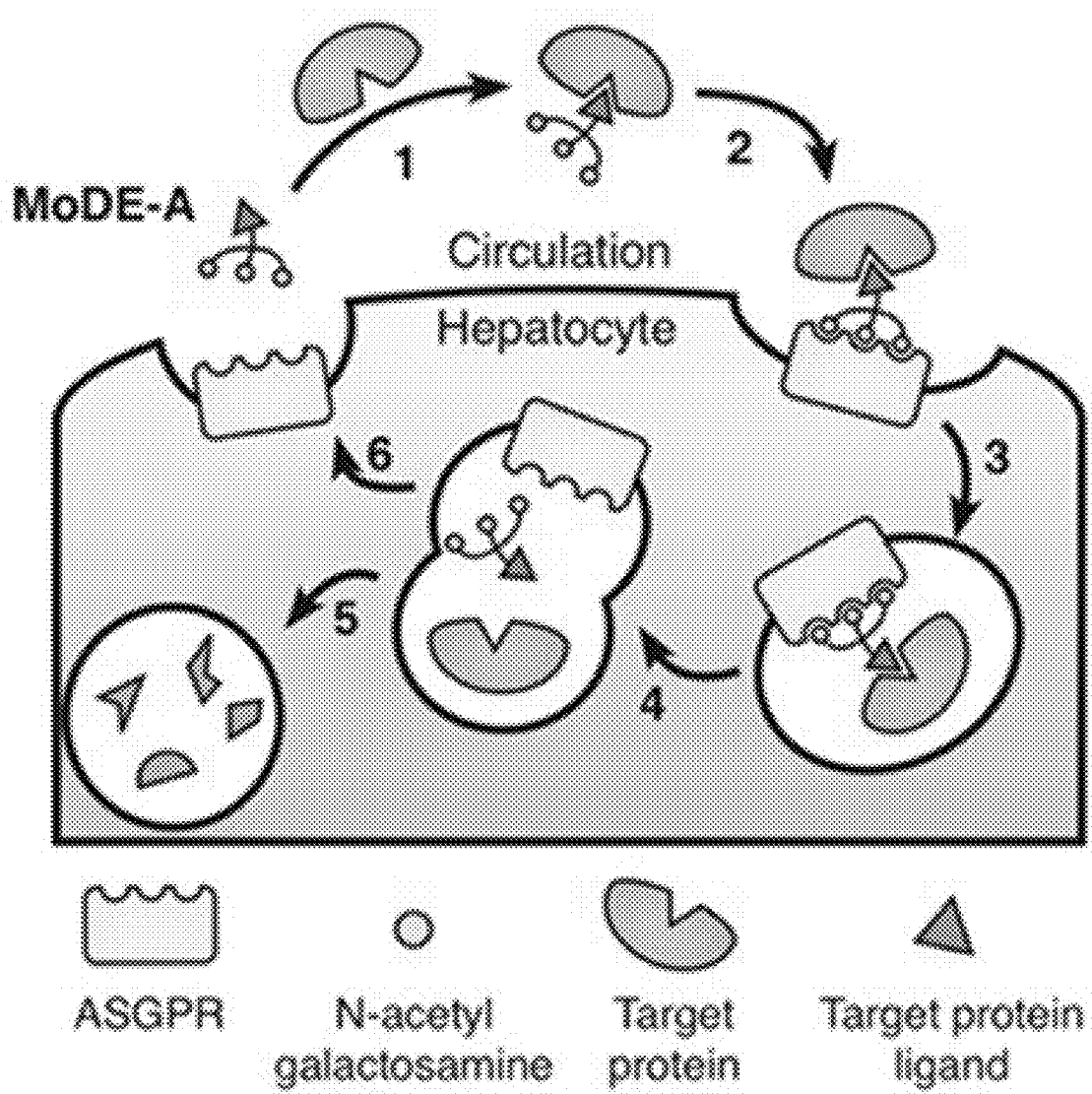
FIG. 1 is a schematic illustration of one mode of action of compounds of Formula I, in accordance with various embodiments. Without wishing to be bound by theory, the mode of action of the compounds here is at least in part as follows: Step 1: MoDE-A binds target protein of interest; Step 2: MoDE-A/protein complex binds ASGPR on hepatocyte; Step 3: ASGPR/MoDE-A/protein ternary complex is endocytosed into hepatocyte; Step 4: Ternary complex dissociates; Step 5: Endocytosed target protein is degraded; and Step 6: ASGPR and MoDE-A are recycled back outside of the cell.
Figure 2A:
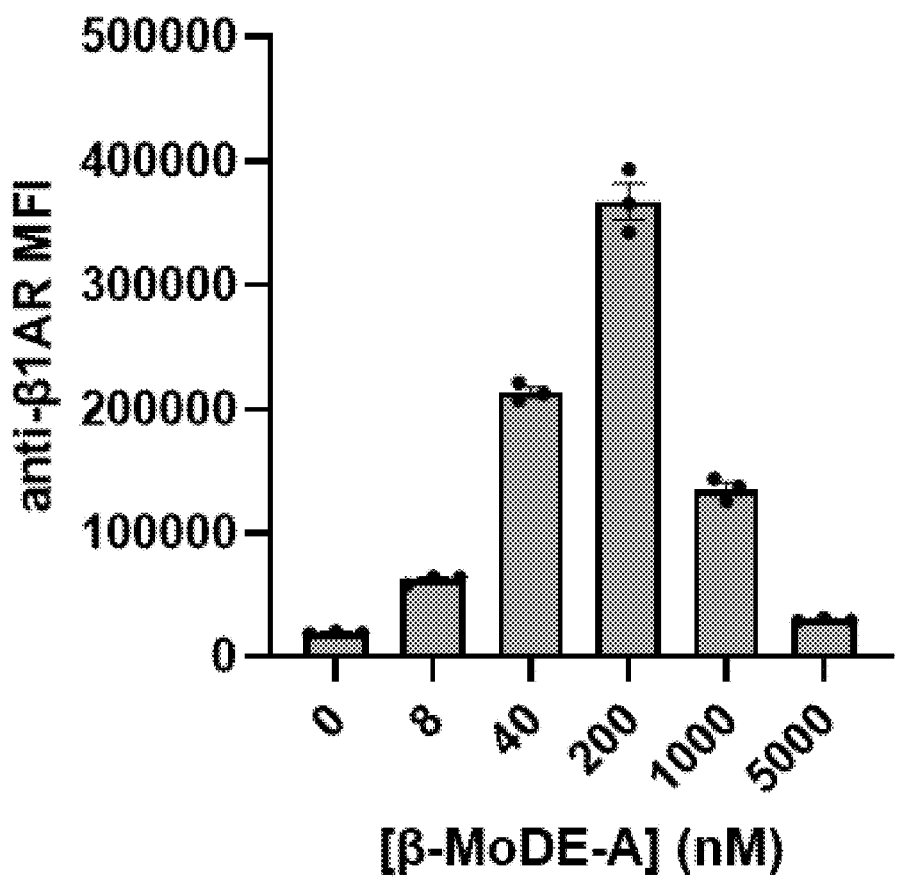
FIGS. 2A-2B show data demonstrating in vitro endocytosis of target antibodies.
Figure 2B:
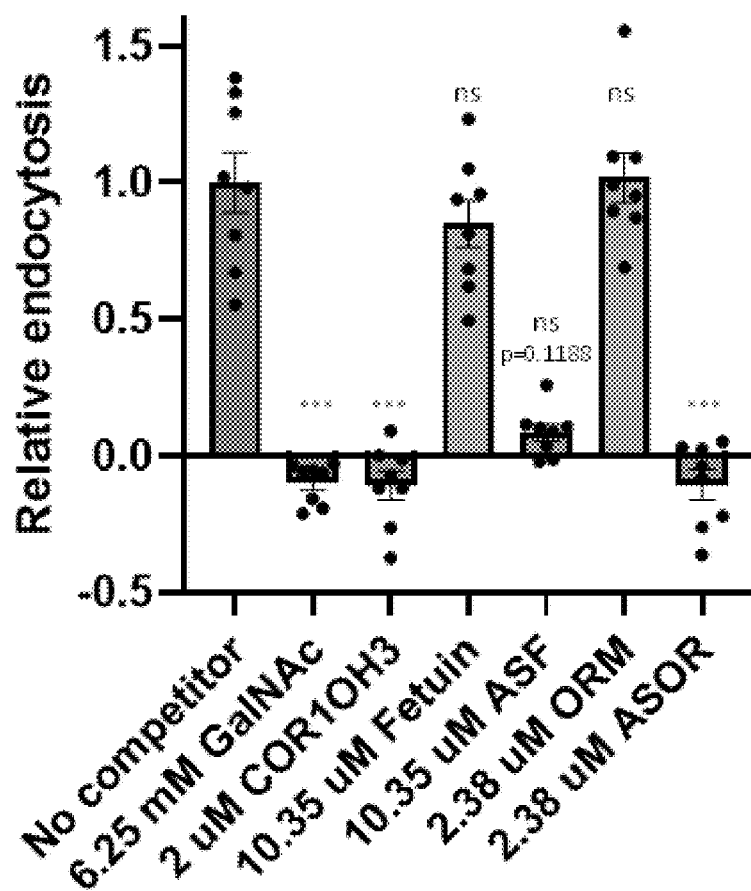
Figure 3A:
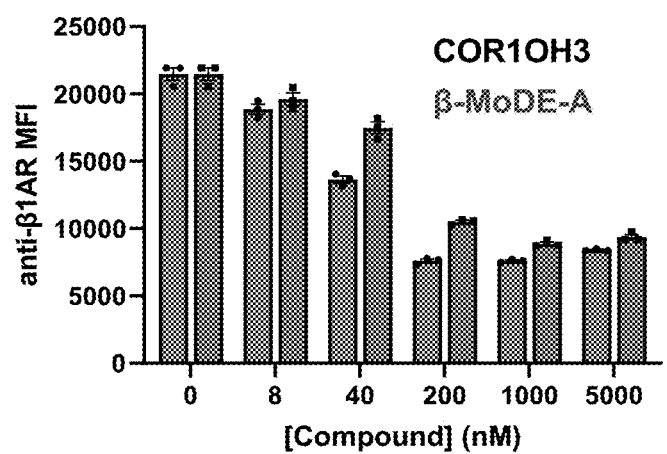
FIGS. 3A-3B show data demonstrating ternary complex formation with target antibodies.
Figure 3B:
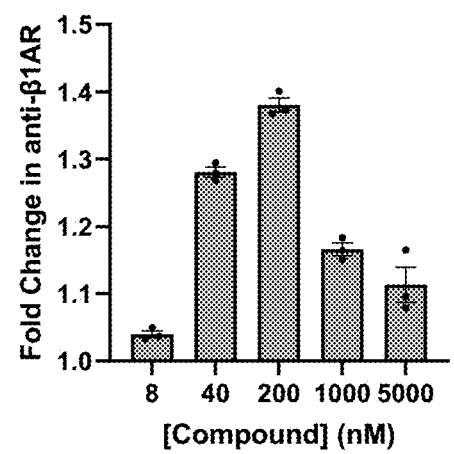

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Definitions

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "aminoalkyl" as used herein refers to an alkyl group as defined herein wherein at least one hydrogen atom in the alkyl group is replaced by nitrogen, forming a primary, secondary, or tertiary amine, depending upon the substitution of the nitrogen. Additionally, an aminoalkyl can have one or more nitrogen atoms between any two carbons in the alkyl chain, forming a secondary or tertiary amine, depending upon the substitution of the nitrogen.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=C=CCH$_2$, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. The term heterocyclyl includes rings where a $CH_2$ group in the ring is replaced by one or more C=O groups, such as found in cyclic ketones, lactones, and lactams. Examples of heterocyclyl groups containing a C=O group include, but are not limited to, β-propiolactam, γ-butyrolactam, δ-valerolactam, and ε-caprolactam, as well as the corresponding lactones. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. A heterocyclyl ring designated $C_{x-y}$ can be any ring containing 'x' members up to 'y' members, including all intermediate integers between 'x' and 'y' and that contains one or more heteroatoms, as defined herein. In a ring designated $C_{x-y}$, all non-heteroatom members are carbon. Heterocyclyl rings designated $C_{x-y}$ can also be polycyclic ring systems, such as bicyclic or tricyclic ring systems. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]

thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halogen alkyl groups, poly-halogen alkyl groups wherein all halogen atoms can be the same or different, and per-halogen alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The terms "epoxy-functional" or "epoxy-substituted" as used herein refers to a functional group in which an oxygen atom, the epoxy substituent, is directly attached to two adjacent carbon atoms of a carbon chain or ring system. Examples of epoxy-substituted functional groups include, but are not limited to, 2,3-epoxypropyl, 3,4-epoxybutyl, 4,5-epoxypentyl, 2,3-epoxypropoxy, epoxypropoxypropyl, 2-glycidoxyethyl, 3-glycidoxypropyl, 4-glycidoxybutyl, 2-(glycidoxycarbonyl)propyl, 3-(3,4-epoxycylohexyl)propyl, 2-(3,4-epoxycyclohexyl)ethyl, 2-(2,3-epoxycylopentyl)ethyl, 2-(4-methyl-3,4-epoxycyclohexyl)propyl, 2-(3,4-epoxy-3-methylcylohexyl)-2-methylethyl, and 5,6-epoxyhexyl.

The term "monovalent" as used herein refers to a substituent connecting via a single bond to a substituted molecule. When a substituent is monovalent, such as, for example, F or Cl, it is bonded to the atom it is substituting by a single bond.

The term "hydrocarbon" or "hydrocarbyl" as used herein refers to a molecule or functional group that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as ($C_a$-$C_b$)hydrocarbyl, wherein a and b are integers and mean having any of a to b number of carbon atoms. For example, ($C_1$-$C_4$)hydrocarbyl means the hydrocarbyl group can be methyl ($C_1$), ethyl ($C_2$), propyl ($C_3$), or butyl ($C_4$), and ($C_0$-$C_b$)hydrocarbyl means in certain embodiments there is no hydrocarbyl group.

The term "solvent" as used herein refers to a liquid that can dissolve a solid, liquid, or gas. Non-limiting examples of solvents are silicones, organic compounds, water, alcohols, ionic liquids, and supercritical fluids.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "room temperature" as used herein refers to a temperature of about 15° C. to 28° C.

The term "standard temperature and pressure" as used herein refers to 20° C. and 101 kPa.

As used herein, the term "composition" or "pharmaceutical composition" refers to a mixture of at least one compound described herein with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect (Emax) achieved within an assay.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids or bases, including inorganic acids or bases, organic acids or bases, solvates, hydrates, or clathrates thereof.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds described herein include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "pharmaceutically acceptable carrier" or "pharmaceutically acceptable excipient" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound described herein within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound(s) described herein, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound(s) described herein, and are physiologically acceptable to the patient. Supplementary active compounds may also be incorporated into the compositions. The "pharmaceutically acceptable carrier" may further include a pharmaceutically acceptable salt of the compound(s) described herein. Other additional ingredients that may be included in the pharmaceutical compositions used with the methods or compounds described herein are known in the art and described, for example in Remington's Pharmaceutical Sciences (Genaro, Ed., Mack Publishing Co., 1985, Easton, PA), which is incorporated herein by reference.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "potency" refers to the dose needed to produce half the maximal response ($ED_{50}$).

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound or compounds as described herein (alone or in combination with another pharmaceutical agent), to a patient, or application or administration of a therapeutic agent to an isolated tissue or cell line from a patient (e.g., for diagnosis or ex vivo applications), who has a condition contemplated herein or a symptom of a condition contemplated herein, with the purpose to cure, heal, alleviate, relieve, alter, remedy, ameliorate, improve or affect a condition contemplated herein, or the symptoms of a condition contemplated herein. Such treatments may be specifically tailored or modified, based on knowledge obtained from the field of pharmacogenomics.

As used herein a, the term “cellular receptor binding moiety” (CRBM) refers to a moiety of the bifunctional compounds described herein that binds to a receptor on a cell capable of degrading circulating proteins in the subject. CRBM’s can be moieties that bind to receptors present in or on hepatocytes. For example, the CRBM can be an asialoglycoprotein receptor (ASGPR), LRPR, LDLR (low density lipoprotein receptor), RcγRI, FcRN, transferrin receptor, macrophage scavenger receptor (e.g., membrane receptors of degradation cells), and the like.

Preparation of Compounds

Compounds of Formula I or otherwise described herein can be prepared by the general schemes described herein, using the synthetic method known by those skilled in the art. The following examples illustrate non-limiting embodiments of the compound(s) described herein and their preparation.

In various embodiments, a compound of Formula I, or a pharmaceutically acceptable salt or N-oxide thereof is provided, and has the structure:

Formula I wherein CON is a connecting linker between $L^A$ and $L^B$, and $L^A$ and $L^B$ are covalently bonded to open valences in CON. $L^A$ is a cellular receptor binding moiety (CRBM). $L^B$ is an anti-$\beta_1$AR binding moiety.

A. Structure of CON Linkers

In various embodiments, CON is a cyclic or acyclic moiety, and can be:

a)

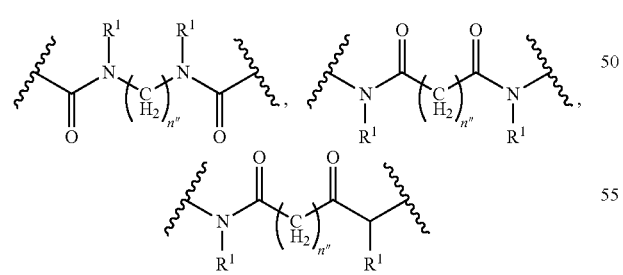

wherein:
$X^2$ is $CH_2$, O, S, $NR^4$, C(O), S(O), $S(O)_2$, $—S(O)_2O$, $—OS(O)_2$, or $OS(O)_2O$;
$X^3$ is O, S, or $NR^4$;

$R^4$ is H, $C_1$-$C_3$ alkyl, $C(=O)C_1$-$C_3$ alkyl, wherein the alkyl groups are optionally substituted by 1-3 hydroxyl groups;

$R^1$ is H or $C_1$-$C_3$ alkyl; and n" is independently an integer ranging from 0 to 20; or b)

wherein each n and n' is independently an integer from 1 to 25; and each n" is independently and integer from 0 to 20; or c)

wherein:

Z and Z' are each independently a bond, $—(CH_2)_i—O—$, $—(CH_2)_i—S—$, $—(CH_2)_i—N(R)—$, each $R^2$ is independently H or $C_1$-$C_3$ alkyl;

each Y is independently a bond, O, S, or N—R;

each i is independently an integer from 0 to 100;

D is or a bond, with the proviso that Z, Z', and D are not each simultaneously bonds;

j is an integer from 1 to 100;

m' is an integer from 1 to 100;

n is an integer from 1 to 100;

$X^1$ is O, S, or N—R;

R is H, or $C_1$-$C_3$ alkyl optionally substituted with 1-3 hydroxyl groups; and each R is H, or $C_1$-$C_3$ alkyl optionally substituted with 1-3 hydroxyl groups; or d) a structure selected from the group consisting of

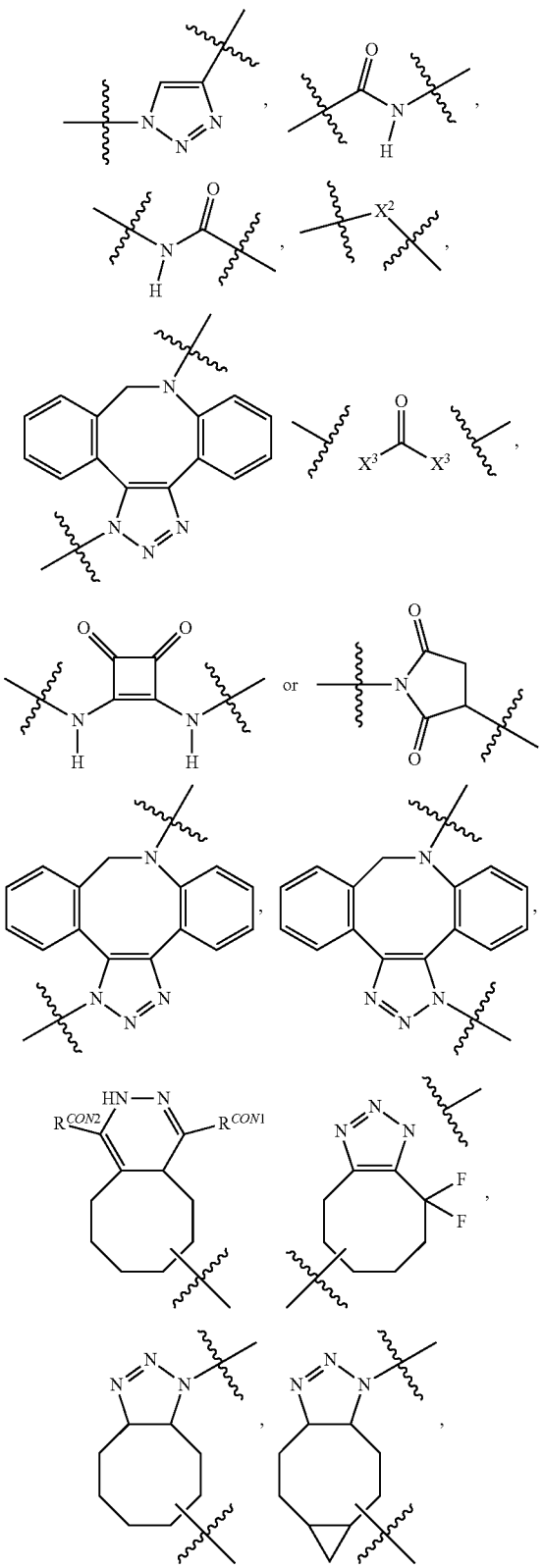

or e) $C_{6-18}$ aryl, $C_{3-18}$ heterocyclyl, $C_{6-18}$ biaryl, or $C_{6-18}$ heterobiaryl, each of which is optionally substituted by 1-6 substituents selected from the group consisting of F, Cl, Br, I, ORG, OC(O)N(RG)$_2$, CN, NO, NO$_2$, ONO$_2$, CF$_3$, OCF$_3$, RG, N(RG)$_2$, SRG, SORG, SO$_2$RG, SO$_2$N(RG)$_2$, and SO$_3$RG, wherein each occurrence of RG is independently H, optionally substituted $C_{1-10}$ alkyl, optionally substituted $C_{3-10}$ cycloalkyl, optionally substituted $C_{6-18}$ aryl, or optionally substituted $C_{5-18}$ heteroaryl.

B. Structures of $L^A$

In various embodiments, $L^A$ is a cellular receptor binding moiety (CRBM). For example, and without limitation, a CRBM can be:

a) an LRP1 (low density lipoprotein receptor-related protein 1) peptide binding moiety having the amino acid sequence:

```
                                                 (SEQ ID NO: 2)
Ac-VKFNKPFVFLNleIEQNTK-NH2, (SEQ ID NO: 3)
VKFNKPFVFLMIEQNTK, (SEQ ID NO: 4)
TWPKHFDKHTFYSILKLGKH-OH, (SEQ ID NO: 5)
TFFYGGSRGKRNNFKTEEY-OH, (SEQ ID NO: 6)
LRKLRKRLLRDADDLLRKLRKRLLRDADDL, (SEQ ID NO: 7)
TEELRVRLASHLRKLRKRLL, (SEQ ID NO: 8)
EAKIEKHNHYQKQLEIAHEKLR,
or (SEQ ID NO: 9)
TFFYGGSRGKRNNFKTEEY;
``` or b) a LDLR (low density lipoprotein receptor) binding moiety having the amino acid sequence:

```
                                                 (SEQ ID NO: 10)
CM-Thz-RLRG-Pen (cyclized c-Pen), (SEQ ID NO: 11)
CMPRLRGC (cyclized C-C), (SEQ ID NO: 12)
HLDCMPRGCFRN (cyclized C-C), (SEQ ID NO: 13)
CQVKSMPRC (cyclized C-C),
```

-continued

CTTPMPRLC (cyclized C-C), (SEQ ID NO: 14)

CKAPQMPRC (cyclized C-C), (SEQ ID NO: 15)

CLNPSMPRC (cyclized C-C), (SEQ ID NO: 16)

CLVSSMPRC (cyclized C-C), (SEQ ID NO: 17)

CLQPMPRLC (cyclized C-C), (SEQ ID NO: 18)

CPVSSMPRC (cyclized C-C), (SEQ ID NO: 19)

CQSPMPRLC (cyclized C-C), (SEQ ID NO: 20)

CLTPMPRLC (cyclized C-C), (SEQ ID NO: 21)

DSGLCMPRLRGCDPR, (SEQ ID NO: 22)

TPSAHAMALQSLSVG, (SEQ ID NO: 23)

Ac-DSGLCMPRLRGCDPR-NH$_2$, (SEQ ID NO: 24)

Pr VH434: Pr-CMPRLRGC-NH$_2$, (SEQ ID NO: 25)

Pr-CMPRLRGC-NH$_2$ (cyclized C-C), (SEQ ID NO: 26)

Pr-CMThzRLRG-Pen-NH$_2$ (cyclized C-Pen), (SEQ ID NO: 27)

Ac-CMPRLGC-NH$_2$ (cyclized C-C), (SEQ ID NO: 28)

Ac-CMPRLRGC-NH$_2$ (cyclized C-C), (SEQ ID NO: 29)

Ac-D-Pen-M-Thz-RLRGC-NH$_2$ (cyclized Pen-C), (SEQ ID NO: 30)

Pr-CM-Thz-RLRG-Pen-NH$_2$ (cyclized c-Pen), (SEQ ID NO: 31)

Pr-CM-Thz-RLR-Sar-Pen-NH$_2$ (cyclized C-Pen), (SEQ ID NO: 32)

Pr-CM-Pip-RLR-Sar-C-NH$_2$ (cyclized C-C), (SEQ ID NO: 33)

Pr-CM-Pip-RLRG-Pen-NH$_2$ (cyclized c-Pen), (SEQ ID NO: 34)
or

Pr-CM-Pip-RLR-Sar-Pen-+-NH$_2$ (cyclized c-Pen), (SEQ ID NO: 35)

wherein any of the LDLR binding moieties containing two cysteine residues or a cysteine and penicillamine residue (Pen) optionally form a cyclic disulfide bond; or c) a FcγRI binding moiety according to the amino acid sequence:

TDT C LMLPLLLG C DEE (cyclized C-C), (SEQ ID NO: 36)

DPI C WYFPRLLG C TTL (cyclized C-C), (SEQ ID NO: 37)

WYP C YIYPRLLG C DGD (cyclized C-C), (SEQ ID NO: 38)

GNI C MLIPGLLG C SYE (cyclized C-C), (SEQ ID NO: 39)

VNS C LLLPNLLG C GDD (cyclized C-C), (SEQ ID NO: 40)

TPV C ILLPSLLG C DTQ (cyclized C-C), (SEQ ID NO: 41)

TVL C SLWPELLG C PPE (cyclized C-C), (SEQ ID NO: 42)

TFS C LMWPWLLG C ESL (cyclized C-C), (SEQ ID NO: 43)

FGT C YTWPWLLG C EGF (cyclized C-C), (SEQ ID NO: 44)

SLF C RLLLTPVG C VSQ (cyclized C-C), (SEQ ID NO: 45)

HLL V LPRGLLG C TTLA (cyclized C-C), (SEQ ID NO: 46)

TSL C SMFPDLLG C FNL (cyclized C-C), (SEQ ID NO: 47)

SHP C GRLPMLLG C AES (cyclized C-C), (SEQ ID NO: 48)

TST C SMVPGPLGAV STW (cyclized C-C), (SEQ ID NO: 49)

KDP C TRWAMLLG C DGE (cyclized C-C), (SEQ ID NO: 50)

IMT C SVYPFLLG C VDK (cyclized C-C), (SEQ ID NO: 51)
or

IHS C AHVMRLLG C WSR (cyclized C-C), (SEQ ID NO: 52)

wherein any of the FcγRI binding moieties containing two cysteine residues optionally form a cyclic disulfide bond; or d) a FcRN binding moiety having the amino acid sequence:

Ac-NH-QRFCTGHFGGLYPCNGP-CONH2 (cyclized C-C), (SEQ ID NO: 53)

Ac-NH-RF-Pen-TGHFG-Sar-NMeLeu-YPC-CONH2 (cyclized C-C), (SEQ ID NO: 54)

or succinic anhydride N—N dimerized SYN1327 (each cyclized C—C), wherein any of the FcRN binding moieties containing two cysteine residues optionally form a cyclic disulfide bond; or e) a transferrin receptor binding group according to the amino acid sequence:

CGGGPFWWWP, (SEQ ID NO: 55)

-continued

CGGGHKYLRW, (SEQ ID NO: 56)

CGGGKRIFMV, (SEQ ID NO: 57)

CGGGKWHYLR, (SEQ ID NO: 58)

THRPPMWSPVWP, (SEQ ID NO: 59)

HAIYPRH, (SEQ ID NO: 60)

THRPPMWSPVWP, (SEQ ID NO: 61)
or

THRPPMWSPVWP; (SEQ ID NO: 62)

f) a macrophage scavenger receptor binding moiety having the amino acid sequence:

LSLERFLRCWSDAPA, (SEQ ID NO: 63)

LERFLRCWSDAPA, (SEQ ID NO: 64)

RFLRCWSDAPA, (SEQ ID NO: 65)

LRCWSDAPA, (SEQ ID NO: 66)

CWSDAPA, (SEQ ID NO: 67)
or

DWFKAFYDKVAEKFKEAF; (SEQ ID NO: 68)

g) a group having the structure:

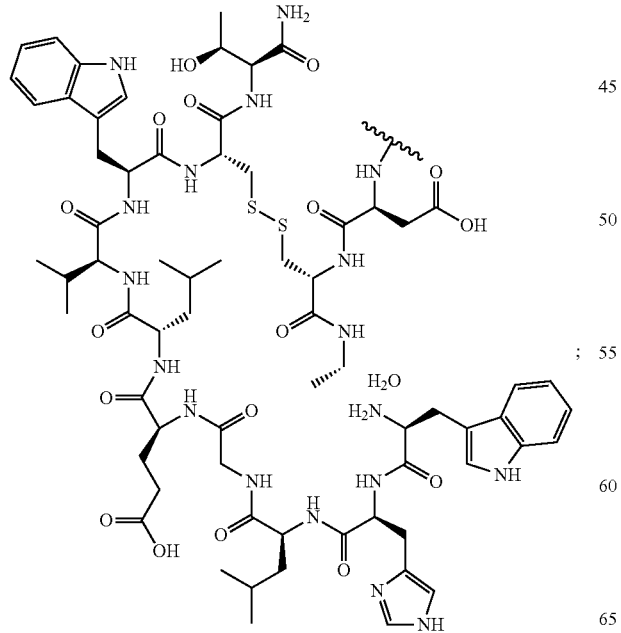

;

or h) a group having the structure:

;

or i) a group having the structure:

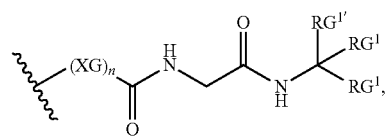

, $RG^{1'}$ is

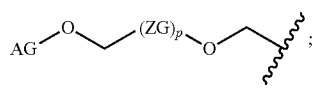

;

each occurrence of $RG^1$ is independently hydrogen or

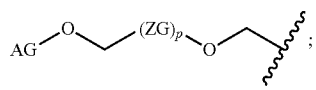

;

each occurrence of XG is independently selected from the group consisting of —CH$_2$—, —C(=O)—, —NH—, and —O—;

each occurrence of ZG is independently selected from the group consisting of —CH$_2$—, —C(=O)—, —NH—, and —O—;

n is an integer from 1 to 100; and p is an integer from 1 to 50.

AG is a monosaccharide, disaccharide, or an oligosaccharide of up to 20 of any monosaccharide units described herein.

Suitable monosaccharides include aldoses such as aldotriose, D-glyceraldehyde, and the like;

aldotetroses such as D-erythrose, D-threose, and the like;

aldopentoses, such as D-ribose, D-arabinose, D-xylose, D-lyxose, and the like;

aldohexoses such as D-allose, D-altrose, D-Glucose, D-Mannose, D-gulose, D-idose, D-galactose and D-talose, and the like;

ketotrioses, such as dihydroxyacetone, and the like;

ketotetroses such as D-erythrulose and the like;

ketopentose such as D-ribulose, D-xylulose, and the like;

ketohexoses such as D-psicone, D-fructose, D-sorbose, D-tagatose, and the like;

aminosugars, such as galactoseamine, sialic acid, N-acetylglucosamine, and the like;

sulfosugars, such as sulfoquinovose, and the like.

Suitable disaccharides include:

sucros, lactose, maltose, trehalose, cellobiose, kojibiose, nigerose, isomaltose, β,β-trehalose, sophorose, laminaribiose, gentiobiose, turanose, maltulose, palatinose, gentiobiluose, mannobiose, melibiose, melibiulose, rutinose, rutinulose, xylobiose, and the like.

In any monosaccharide, disaccharide, or oligosaccharide described herein, one or more of the hydroxy (OH) groups in the particular sugar can be replaced with an $NRG^2RG^3$ group, wherein $RG^2$ and $RG^3$ are each independently selected from the group consisting of hydrogen and —C(=O)R, which is optionally substituted by 1-5 groups selected from the group consisting of halogen, optionally substituted $C_{1-10}$ alkyl, optionally substituted $C_{1-10}$ alkoxy, optionally substituted $C_{1-10}$ aminoalkyl, and combinations thereof, or $RG^2$ and $RG^3$ taken together with the nitrogen atom to which they are attached, form a C5 heterocycle that is optionally substituted by 1-5 substituents selected from the group consisting of optionally substituted $C_{1-10}$ alkyl, optionally substituted $C_{1-10}$ alkoxy, optionally substituted $C_{1-10}$ aminoalkyl, optionally substituted $C_{6-10}$ aryl, optionally substituted $C_{5-10}$ heteroaryl, halogen, and combinations thereof. Each occurrence of RG is independently H, optionally substituted $C_{1-10}$ alkyl, optionally substituted $C_{3-10}$ cycloalkyl, optionally substituted $C_{6-18}$ aryl, or optionally substituted $C_{5-18}$ heteroaryl;

In any monosaccharide, disaccharide, or oligosaccharide described herein, the sugar (AG) in

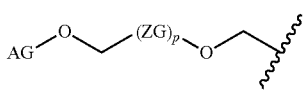

is connected through the anomeric carbon on the sugar.

In one embodiment, AG has the structure:

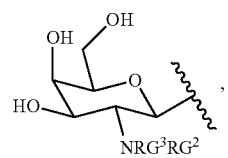

and $(ZG)_p$ has the structure:

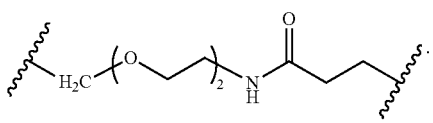

In various embodiments, $(XG)_n$ has a structure selected from the group consisting of —O—$(CH_2)_3$—, —NH—$(CH_2CH_2O)_3$—$CH_2$—, and =N*(C=O)$(CH_2)_2$C(=O)NHCH$_2$CH$_2$—(OCH$_2$CH$_2$)$_4$—, wherein =N* is a ring nitrogen in heterocyclic ring system; or combinations of the groups a) through i).

In the amino acid sequences herein, non-standard amino acids are defined as follows:

| Non-standard Amino Acid | Structure | Name |
| --- | --- | --- |
| Pen | 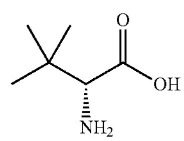 | penicillamine |
| Thz | 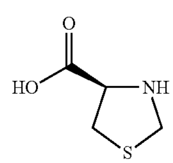 | L-thiazolidine-4-carboxylic acid |
| Sar | 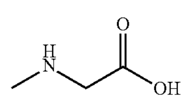 | sarcosine |
| Pip | 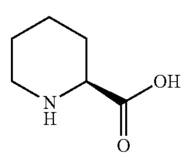 | L-pipecolic acid |
| Nleu | 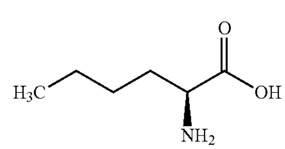 | norleucine |

| Non-standard Amino Acid | Structure | Name |
|---|---|---|
| NMeLeu | 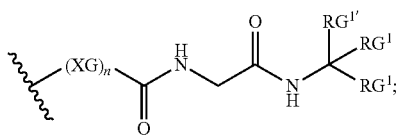 | N-methyl leucine |

C. Structures of $L^B$

In various embodiments, $L^B$ is an anti-$\beta_1$AR (adrenergic receptor) antibody binding moiety with the structure

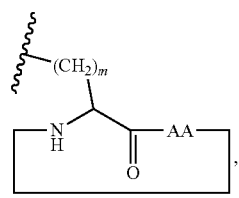

wherein AA is an amino acid sequence at least 80% homologous to SEQ ID NO: 1, DEARRCYND-PKCSDFVQ (SEQ ID NO:1), and m is an integer from 2 to 10. By at least 80% homologous it is meant that an amino acid sequence with an anti-$\beta_1$AR antibody binding region that is 80% homologous to SEQ ID NO:1, even if the amino acid sequence contains more residues, including synthetically modified residues, than SEQ ID NO: 1.

In various embodiments, the compound of Formula I has the structure:

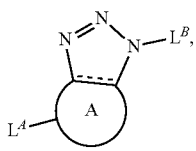

Formula Ia wherein:

- - - - - is a carbon-carbon single or double bond.

A is a $C_{6-18}$ aryl, $C_{3-18}$ heterocyclyl, $C_{6-18}$ biaryl, or $C_{6-18}$ heterobiaryl, each of which is optionally substituted by 1-6 substituents selected from the group consisting of F, Cl, Br, I, ORG, OC(O)N(RG)$_2$, CN, NO, NO$_2$, ONO$_2$, CF$_3$, OCF$_3$, RG, N(RG)$_2$, SR, SORG, SO$_2$RG, SO$_2$N(RG)$_2$, and SO$_3$RG;

$L^A$ is an asialoglycoprotein receptor (ASGPR) binding moiety with the structure:

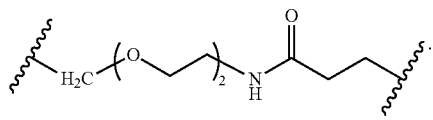

$L^B$ is an anti-$\beta_1$AR binding moiety with the structure

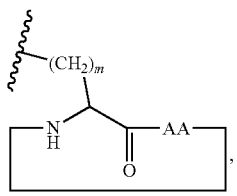

AA is an amino acid sequence at least 80% homologous to SEQ ID NO: 1;

$RG^{1'}$ is

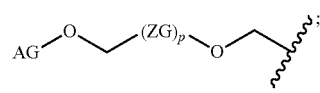

each occurrence of $RG^1$ is independently hydrogen or

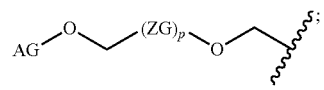

$(ZG)_p$ has the structure:

In various embodiments, $(XG)_n$ has a structure selected from the group consisting of —O—(CH$_2$)$_3$—, —NH—(CH$_2$CH$_2$O)$_3$—CH$_2$—, and =N*(C=O)(CH$_2$)$_2$C(=O)NHCH$_2$CH$_2$—(OCH$_2$CH$_2$)$_4$—, wherein =N* is a ring nitrogen in a heterocyclic ring system;

AG is an aminosaccharide;

each occurrence of RG is independently H, optionally substituted $C_{1-10}$ alkyl, optionally substituted $C_{3-10}$ cycloalkyl, optionally substituted $C_{6-18}$ aryl, or optionally substituted $C_{5-18}$ heteroaryl;

each occurrence of XG is independently selected from the group consisting of —CH$_2$—, —C(=O)—, —NH—, and —O—;

each occurrence of ZG is independently selected from the group consisting of —CH$_2$—, —C(=O)—, —NH—, and —O—;

m is an integer from 2 to 10;

n is an integer from 1 to 100; and p is an integer from 1 to 50.

In the compound of Formula Ia, A is a ring or ring system that can contain multiple rings. Thus A can be a ring system containing two, three, four, or more rings fused together or bonded together as in, for example, a bi-aryl ring system. Heterocyclyl A rings can be aromatic or can contain aliphatic carbon or nitrogen atoms in some portion of the ring or rings in A.

In various embodiments, AA has the sequence DEARRCYNDPKCSDFVQ (SEQ ID NO:1).

Asiaglycoprotein receptors (ASGR1) bind asiaglycoproteins and other glycoproteins from which a sialic acid has been removed, exposing galactose residues. In various embodiments, $L^B$ has the structure:

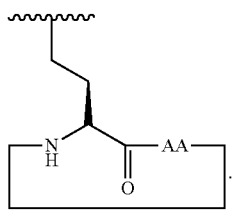

In various embodiments, AG has the structure:

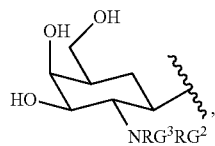

wherein $RG^2$ and $RG^3$ are each independently selected from the group consisting of hydrogen and —C(=O)R, which is optionally substituted by 1-5 groups selected from the group consisting of halogen, optionally substituted $C_{1-10}$ alkyl, optionally substituted $C_{1-10}$ alkoxy, optionally substituted $C_{1-10}$ aminoalkyl, and combinations thereof, or $RG^2$ and $RG^3$ taken together with the nitrogen atom to which they are attached, form a C5 heterocycle that is optionally substituted by 1-5 substituents selected from the group consisting of optionally substituted $C_{1-10}$ alkyl, optionally substituted $C_{1-10}$ alkoxy, optionally substituted $C_{1-10}$ aminoalkyl, optionally substituted $C_{6-10}$ aryl, optionally substituted $C_{5-10}$ heteroaryl, halogen, and combinations thereof. In various embodiments, $RG^2$ is hydrogen and $RG^3$ is C(=O)CH$_3$.

AG, in various embodiments, includes other galactosyl analogs that bind to ASGR.

In various embodiments, $(Z)_p$ has the structure:

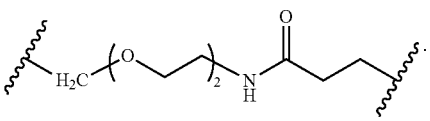

In various embodiments, $(XG)_n$ has a structure selected from the group consisting of —O—(CH$_2$)$_3$—, —NH—(CH$_2$CH$_2$O)$_3$—CH$_2$—, and =N*(C=O)(CH$_2$)$_2$C(=O)NHCH$_2$CH$_2$—(OCH$_2$CH$_2$)$_4$—, wherein =N* is a ring nitrogen in A.

In various embodiments, AA is a (6,12) cyclic peptide in which the cysteine residues at positions 6 and 12 in AA form a disulfide bond. In various embodiments, AA is at least 95% homologous to SEQ ID NO:1. In various embodiments, AA is an amino acid sequence of SEQ ID NO: 1.

In various embodiments, the compound of Formula Ia has the structure:

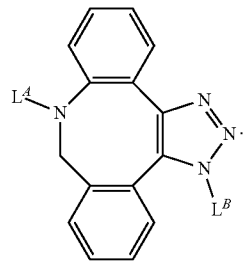

In various embodiments, the compound of Formula Ia has the structure:

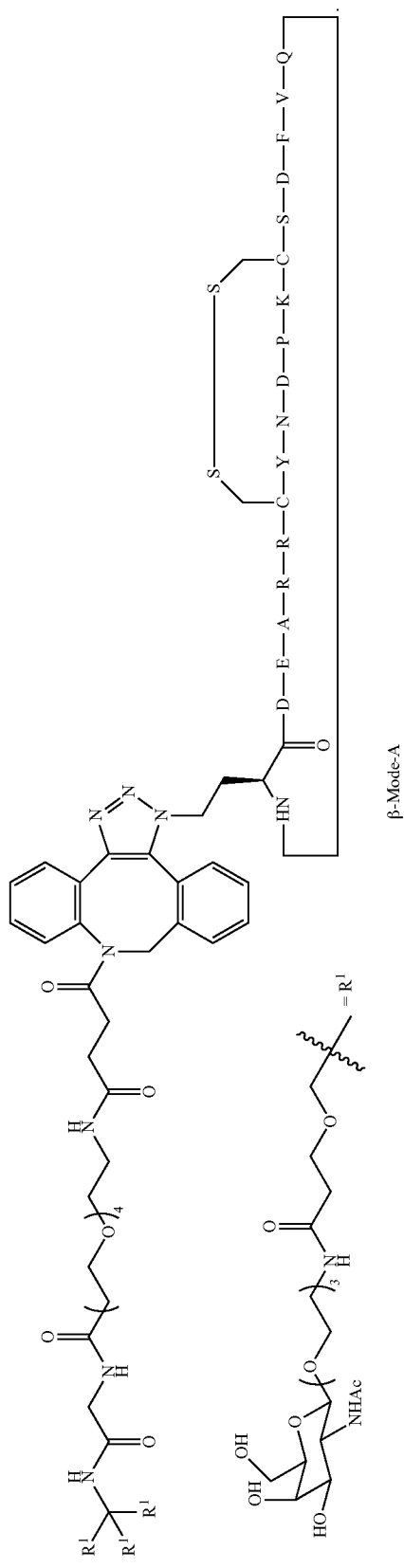

The presence of auto-antibodies against the $\beta_1$-AR can be used to identify populations of patients that are particularly at risk after heart failure. In certain embodiments, chronic activation of the $\beta_1$-AR can result in reduced cardiac function and weakening of the cardiac structure. Autoantibodies that remain functionally active and are directed against (and stimulate) cardiac $\beta_1$-AR are often present in patients suffering from DCM, and the continued presence of these anti $\beta_1$-AR antibodies is frequently associated with cardiac disorders such as ventricular arrhythmias, sudden cardiac death, and increased cardiovascular mortality. In various embodiments, and without wishing to be bound by theory, compounds of Formula I can bind to these anti $\beta_1$-AR antibodies through the $L^B$ moiety in the compound of Formula I. In various embodiments, and without being bound by theory, by bringing the ASGPR into proximity of these antibodies through binding of the $L^A$ moiety to ASGPR, endocytosis and/or degradation of these harmful antibodies can be achieved.

The compounds described herein can possess one or more stereocenters, and each stereocenter can exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound(s) described herein, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compound(s) described herein can exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compound(s) described herein are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

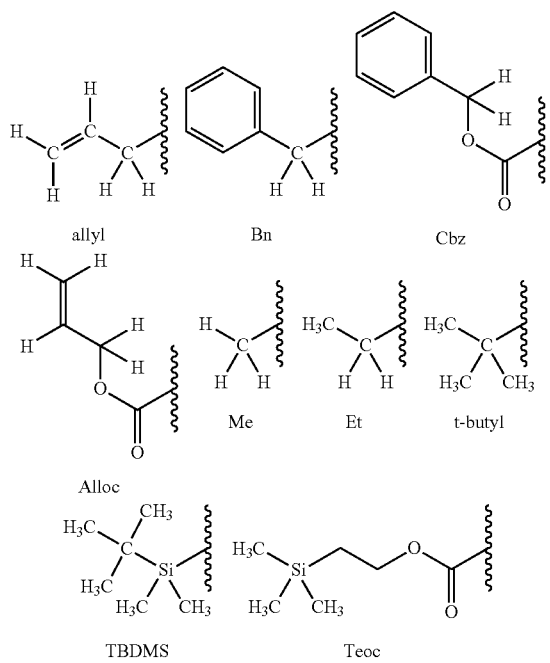

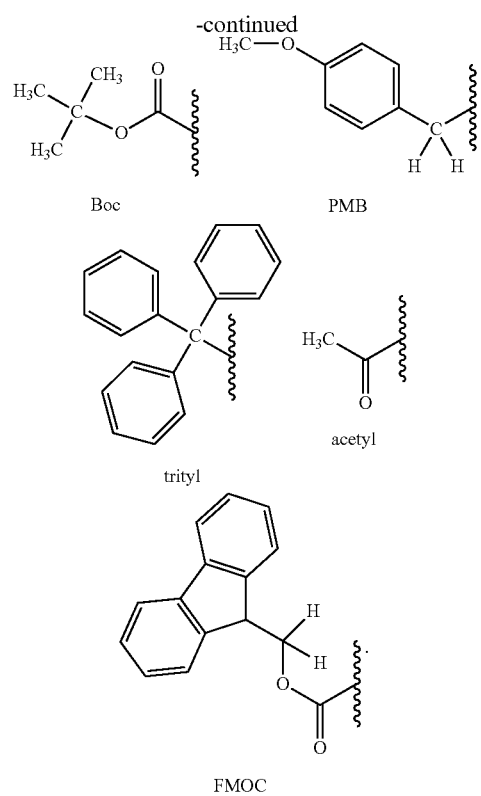

Other protecting groups, plus a detailed description of techniques applicable to the creation of protecting groups and their removal are described in Greene & Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

Compositions

The compositions containing the compound(s) described herein include a pharmaceutical composition comprising at least one compound as described herein and at least one pharmaceutically acceptable carrier. In certain embodiments, the composition is formulated for an administration route such as oral or parenteral, for example, transdermal, transmucosal (e.g., sublingual, lingual, (trans)buccal, (trans)urethral, vaginal (e.g., trans- and perivaginally), (intra)nasal and (trans)rectal, intravesical, intrapulmonary, intraduodenal, intragastrical, intrathecal, subcutaneous, intramuscular, intradermal, intra-arterial, intravenous, intrabronchial, inhalation, and topical administration.

Methods of Treatment

The disclosure includes a method of preventing, treating, and/or ameliorating heart failure using the compounds of Formula I. Non-limiting examples of heart failure include dilated cardiomyopathy, hypertrophic cardiomyopathy, and/or restrictive cardiomyopathy. Cardiomyopathy can be the result of a variety of conditions including, long-term high blood pressure, heart tissue damage due to heart attack, heart valve malfunction, COVID-19 infection, hemochromatosis, amyloidosis, sarcoidosis, and/or chemotherapy drugs, and the like. The method includes administering a composition comprising a therapeutically effective amount of a compound of Formula I, and at least one pharmaceutically acceptable carrier. In various embodiments, the heart failure is dilated cardiomyopathy (DCM).

In various embodiments, the composition is administered by a route selected from the group consisting of oral, transdermal, transmucosal, (intra)nasal, (trans)rectal, intravesical, intrapulmonary, intraduodenal, intragastrical, intrathecal, subcutaneous, intramuscular, intradermal, intraarterial, intravenous, intrabronchial, inhalation, and topical.

In various embodiments, the subject is a mammal. In various embodiments, the subject is human.

The methods described herein include administering to the subject a therapeutically effective amount of at least one compound described herein, which is optionally formulated in a pharmaceutical composition. In various embodiments, a therapeutically effective amount of at least one compound described herein present in a pharmaceutical composition is the only therapeutically active compound in a pharmaceutical composition. In certain embodiments, the method further comprises administering to the subject an additional therapeutic agent that treats heart failure.

In certain embodiments, administering the compound(s) described herein to the subject allows for administering a lower dose of the additional therapeutic agent as compared to the dose of the additional therapeutic agent alone that is required to achieve similar results in treating a heart failure in the subject. For example, in certain embodiments, the compound(s) described herein enhance(s) the activity of the additional therapeutic compound, thereby allowing for a lower dose of the additional therapeutic compound to provide the same effect.

In certain embodiments, the compound(s) described herein and the therapeutic agent are co-administered to the subject. In other embodiments, the compound(s) described herein and the therapeutic agent are coformulated and co-administered to the subject.

In certain embodiments, the subject is a mammal. In other embodiments, the mammal is a human.

Combination Therapies

The compounds useful within the methods described herein can be used in combination with one or more additional therapeutic agents useful for treating heart failure. These additional therapeutic agents may comprise compounds that are commercially available or synthetically accessible to those skilled in the art. These additional therapeutic agents are known to treat or reduce the symptoms of heart failure.

In various embodiments, compounds of Formula I can be administered either sequentially or concurrently with $\beta_1$-AR blockers, such as acebutolol, atenolol, betaxolol, bisoprolol, metoprolol, nadolol, propranolol, sotalol, and/or caredilol, and the like. In some embodiments, when $\beta_1$-AR blockers are co-administered with compounds of Formula I, they can be administered at a lowered dose than if the $\beta_1$-AR blocker was administered as a monotherapy. In various embodiments, the $\beta_1$-AR blocker is administered at 90%, 80%, 70%, 60%, 50%, 40%, 30%, 20%, 10%, or 5% of the minimum approved therapeutic dose for the particular $\beta_1$-AR blocker used in therapy in combination with a compound of Formula I. In various embodiments, co-administration of $\beta_1$-AR blockers and the compound of Formula I results in fewer, less severe, or no side effects associated with the use of $\beta_1$-AR blockers.

In certain embodiments, the compounds described herein can be used in combination with radiation therapy. In other embodiments, the combination of administration of the compounds described herein and application of radiation therapy is more effective in treating, ameliorating, or preventing heart failure than application of radiation therapy by itself. In yet other embodiments, the combination of administration of the compounds described herein and application of radiation therapy allows for use of lower amount of radiation therapy in treating the subject.

In various embodiments, a synergistic effect is observed when a compound as described herein is administered with one or more additional therapeutic agents or compounds. A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a heart failure. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions described herein to a patient, preferably a mammal, more preferably a human, may be carried out using known procedures, at dosages and for periods of time effective to treat heart failure in the patient. An effective amount of the therapeutic compound necessary to achieve a therapeutic effect may vary according to factors such as the state of the disease or disorder in the patient; the age, sex, and weight of the patient; and the ability of the therapeutic compound to treat heart failure in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound described herein is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds described herein employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the compound(s) described herein are dictated by and directly dependent on (a) the unique characteristics of the therapeutic compound and the particular therapeutic effect to be achieved, and (b) the limitations inherent in the art of compounding/formulating such a therapeutic compound.

In certain embodiments, the compositions described herein are formulated using one or more pharmaceutically acceptable excipients or carriers. In certain embodiments, the pharmaceutical compositions described herein comprise a therapeutically effective amount of a compound described herein and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions described herein are administered to the patient in dosages that range from one to five times per day or more. In other embodiments, the compositions described herein are administered to the patient in range of dosages that include, but are not limited to, once every day, every two, days, every three days to once a week, and once every two weeks. It is readily apparent to one skilled in the art that the frequency of administration of the various combination compositions described herein varies from individual to individual depending on many factors including, but not limited to, age, disease or disorder to be treated, gender, overall health, and other factors. Thus, administration of the compounds and compositions described herein should not be construed to be limited to any particular dosage regime and the precise dosage and composition to be administered to any patient is determined by the attending physician taking all other factors about the patient into account.

The compound(s) described herein for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 350 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween. In various embodiments, compounds of Formula I are administered at a dose of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20 mg/kg.

In some embodiments, the dose of a compound described herein is from about 1 mg and about 2,500 mg. In some embodiments, a dose of a compound described herein used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, a composition as described herein is a packaged pharmaceutical composition comprising a container holding a therapeutically effective amount of a compound described herein, alone or in combination with a second pharmaceutical agent; and instructions for using the compound to treat, prevent, or reduce one or more symptoms of heart failure in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions described herein include oral, nasal, rectal, intravaginal, parenteral, buccal, sublingual or topical. The compounds for use in the compositions described herein can be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In various embodiments, the compounds of Formula I are administered by intravenous administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions described herein are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compound(s) described herein can be in the form of tablets or capsules prepared by conventional means with pharmaceutically acceptable excipients such as binding agents (e.g., polyvinylpyrrolidone, hydroxypropylcellulose or hydroxypropyl methylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Compositions as described herein can be prepared, packaged, or sold in a formulation suitable for oral or buccal administration. A tablet that includes a compound as described herein can, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, dispersing agents, surface-active agents, disintegrating agents, binding agents, and lubricating agents.

Suitable dispersing agents include, but are not limited to, potato starch, sodium starch glycollate, poloxamer 407, or poloxamer 188. One or more dispersing agents can each be individually present in the composition in an amount of about 0.01% w/w to about 90% w/w relative to weight of the dosage form. One or more dispersing agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Surface-active agents (surfactants) include cationic, anionic, or non-ionic surfactants, or combinations thereof. Suitable surfactants include, but are not limited to, behentrimonium chloride, benzalkonium chloride, benzethonium chloride, benzododecinium bromide, carbethopendecinium bromide, cetalkonium chloride, cetrimonium bromide, cetrimonium chloride, cetylpyridine chloride, didecyldimethylammonium chloride, dimethyldioctadecylammonium bromide, dimethyldioctadecylammonium chloride, domiphen bromide, lauryl methyl gluceth-10 hydroxypropyl dimonium chloride, tetramethylammonium hydroxide, thonzonium bromide, stearalkonium chloride, octenidine dihydrochloride, olaflur, N-oleyl-1,3-propanediamine, 2-acrylamido-2-methylpropane sulfonic acid, alkylbenzene sulfonates, ammonium lauryl sulfate, ammonium perfluorononanoate, docusate, disodium cocoamphodiacetate, magnesium laureth sulfate, perfluorobutanesulfonic acid, perfluorononanoic acid, perfluorooctanesulfonic acid, perfluorooctanoic acid, potassium lauryl sulfate, sodium alkyl sulfate, sodium dodecyl sulfate, sodium laurate, sodium laureth sulfate, sodium lauroyl sarcosinate, sodium myreth sulfate, sodium nonanoyloxybenzenesulfonate, sodium pareth sulfate, sodium stearate, sodium sulfosuccinate esters, cetomacrogol 1000, cetostearyl alcohol, cetyl alcohol, cocamide diethanolamine, cocamide monoethanolamine, decyl glucoside, decyl polyglucose, glycerol monostearate, octylphenoxypolyethoxyethanol CA-630, isoceteth-20, lauryl glucoside, octylphenoxypolyethoxyethanol P-40, Nonoxynol-9, Nonoxynols, nonyl phenoxypolyethoxylethanol (NP-40), octaethylene glycol monododecyl ether, N-octyl beta-D-thioglucopyranoside, octyl glucoside, oleyl alcohol, PEG-10 sunflower glycerides, pentaethylene glycol monododecyl ether, polidocanol, poloxamer, poloxamer 407, polyethoxylated tallow amine, polyglycerol polyricinoleate, polysorbate, polysorbate 20, polysorbate 80, sorbitan, sorbitan monolaurate, sorbitan monostearate, sorbitan tristearate, stearyl alcohol, surfactin, Triton X-100, and Tween 80. One or more surfactants can each be individually present in the composition in an amount of about 0.01% w/w to about 90% w/w relative to weight of the dosage form. One or more surfactants can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable diluents include, but are not limited to, calcium carbonate, magnesium carbonate, magnesium oxide, sodium carbonate, lactose, microcrystalline cellulose, calcium phosphate, calcium hydrogen phosphate, and sodium phosphate, Cellactose® 80 (75% α-lactose monohydrate and 25% cellulose powder), mannitol, pre-gelatinized starch, starch, sucrose, sodium chloride, talc, anhydrous lactose, and granulated lactose. One or more diluents can each be individually present in the composition in an amount of about 0.01% w/w to about 90% w/w relative to weight of the dosage form. One or more diluents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable granulating and disintegrating agents include, but are not limited to, sucrose, copovidone, corn starch, microcrystalline cellulose, methyl cellulose, sodium starch glycollate, pregelatinized starch, povidone, sodium carboxy methyl cellulose, sodium alginate, citric acid, croscarmellose sodium, cellulose, carboxymethylcellulose calcium, colloidal silicone dioxide, crospovidone and alginic acid. One or more granulating or disintegrating agents can each be individually present in the composition in an amount of about 0.01% w/w to about 90% w/w relative to weight of the dosage form. One or more granulating or disintegrating agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable binding agents include, but are not limited to, gelatin, acacia, pre-gelatinized maize starch, polyvinylpyrrolidone, anhydrous lactose, lactose monohydrate, hydroxypropyl methylcellulose, methylcellulose, povidone, polyacrylamides, sucrose, dextrose, maltose, gelatin, polyethylene glycol. One or more binding agents can each be individually present in the composition in an amount of about 0.01% w/w to about 90% w/w relative to weight of the dosage form. One or more binding agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable lubricating agents include, but are not limited to, magnesium stearate, calcium stearate, hydrogenated castor oil, glyceryl monostearate, glyceryl behenate, mineral oil, polyethylene glycol, poloxamer 407, poloxamer 188, sodium laureth sulfate, sodium benzoate, stearic acid, sodium stearyl fumarate, silica, and talc. One or more lubricating agents can each be individually present in the composition in an amount of about 0.01% w/w to about 90% w/w relative to weight of the dosage form. One or more lubricating agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Tablets can be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Tablets can also be enterically coated such that the coating begins to dissolve at a certain pH, such as at about pH 5.0 to about pH 7.5, thereby releasing a compound as described herein. The coating can contain, for example, EUDRAGIT® L, S, FS, and/or E polymers with acidic or alkaline groups to allow release of a compound as described herein in a particular location, including in any desired section(s) of the intestine. The coating can also contain, for example, EUDRAGIT® RL and/or RS polymers with cationic or neutral groups to allow for time controlled release of a compound as described herein by pH-independent swelling.

Parenteral Administration

For parenteral administration, the compounds as described herein may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as such as lauryl, stearyl, or oleyl alcohols, or similar alcohol.

Additional Administration Forms

Additional dosage forms suitable for use with the compound(s) and compositions described herein include dosage forms as described in U.S. Pat. Nos. 6,340,475; 6,488,962; 6,451,808; 5,972,389; 5,582,837; and 5,007,790. Additional dosage forms suitable for use with the compound(s) and compositions described herein also include dosage forms as described in U.S. Patent Applications Nos. 20030147952; 20030104062; 20030104053; 20030044466; 20030039688; and 20020051820. Additional dosage forms suitable for use with the compound(s) and compositions described herein also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations described herein can be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use with the method(s) described herein may be administered in the form of microparticles, for example, by injection or in the form of wafers or discs by implantation.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions described herein. Thus, single unit dosage forms suitable for oral administration, such as tablets, capsules, gelcaps, and caplets, that are adapted for controlled-release are encompassed by the compositions and dosage forms described herein.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" is defined herein as a compound or compounds, including, but not limited to, polymers, polymer matrices, gels, permeable membranes, liposomes, or microspheres or a combination thereof that facilitates the controlled-release of the active ingredient. In one embodiment, the compound(s) described herein are administered to a patient, alone or in combination with another pharmaceutical agent, using a sustained release formulation. In one embodiment, the compound(s) described herein are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound described herein depends on the age, sex and weight of the patient, the current medical condition of the patient and the progression of heart failure in the patient being treated. The skilled artisan is able to determine appropriate dosages depending on these and other factors.

A suitable dose of a compound described herein can be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the compound(s) described herein is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced to a level at which the improved disease is retained. In certain embodiments, patients require intermittent treatment on a long-term basis upon any recurrence of symptoms and/or infection.

The compounds described herein can be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Examples

Various embodiments of the present application can be better understood by reference to the following Examples which are offered by way of illustration. The scope of the present application is not limited to the Examples given herein.

Materials and Methods
Biological Materials and Methods

Data was analyzed and visualized using GraphPad Prism 7.0a software. All statistical tests were two-sided and significance was assessed at $p<0.05$.

Cell Culture

HepG2 cells were purchased from ATCC. Cells were cultured in Dulbecco's Modified Eagle Medium (DMEM) (Gibco, Ref 11995-065) supplemented with 10% FBS (Millipore Sigma, TMS-013-B) and penicillin/streptomycin (ThermoFisher, 10378016). Assays were carried out in sterile-filtered opti-MEM (Gibco 31985-070) supplemented with 0.1% BSA (Sigma, A9418) and penicillin/streptomycin. Cells were grown to greater than 90% confluency before beginning all experiments. Cells were passaged by first aspirating the media, followed by treatment with trypsin (0.25%, Gibco ref 25200) and incubation at 37° C. until cells began to detach from the plate (approximately 5 minutes). Cell aggregates were dispersed by passing the cell solution through a 200 µL pipette tip several times.

Flow Cytometry

Figure 9:
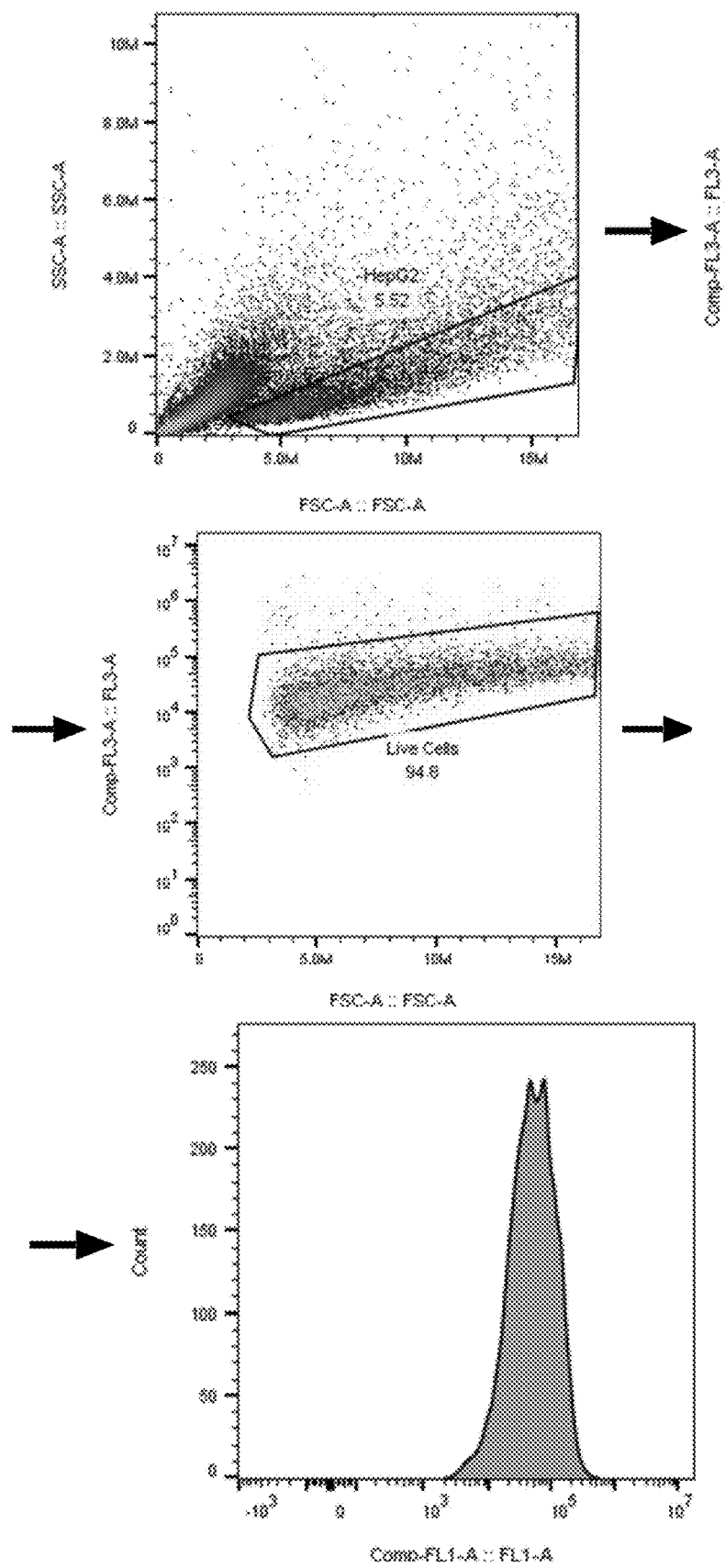
FIG. 9 shows an illustrative flow cytometry gating strategy contemplated within the disclosure.

Flow experiments were performed using an Accuri C6 flow cytometer using BD Accuri C6 software. Data was analyzed using FlowJo version 10.6.1 for Windows. Each cell population from which MFI was calculated contained at least 1,000 live cells. A representative flow cytometry gating strategy is shown in FIG. 9.

Biological Reagents

Asialofetuin (Sigma, A4781), fetuin (Sigma, F2379), and ORM (Sigma, G9885) were each resuspended at a concentration of 1 mg/mL in assay media (opti-MEM+0.1% BSA). ASOR was prepared from ORM using a solid-phase neuraminidase kit (Sigma, N5254). 15 mg of ORM was treated with immobilized neuraminidase corresponding to 0.5 units. The kit defines 1 unit as the amount of enzyme necessary to remove 1.0 µmol of sialic acid from bovine submaxillary mucin in 1 minute at pH 5 and 37° C. Desialylation was carried out in a buffer of 100 mM sodium acetate and 2 mM calcium chloride (pH 5) according to manufacturer instructions. Briefly, the slurry of neuraminidase beads was placed on filter paper, then dried over vacuum. The filtrate was washed with DI water 10 times before the beads were added to the ORM solution. The neuraminidase beads were then incubated with ORM on a rotator for 1 hour at 37° C., followed by filtration to remove the neuraminidase and dialysis against PBS overnight at 4° C. Removal of sialic acid was confirmed using a sialic acid assay kit (Sigma, MAK314). In vitro experimentation with $\alpha\beta_1$-MoDE-A was performed using monoclonal anti-$\beta_1$AR antibody 23-6-7, graciously provided by Martin Ungerer and colleagues. The antibody was fluorescently labeled using an AF488 antibody labeling kit (Thermo, A20181). A single tube of dye was used to label 100 µg of antibody at a time. Unreacted dye was removed by using size exclusion zebra spin columns with a 7k MWCO filter (Thermo, 89878).

Endocytosis Assays

HepG2 cells were grown to confluency in a 96 well plate and washed with PBS. Cells were treated with premixed $\alpha\beta_1$-MoDE-A (8-5000 nM final concentration) and AF488-labeled anti-$\beta_1$AR (100 nM final concentration) at 37° C. in an incubator for twelve hours. In assays including competitive binders of ASGPR or anti-$\beta_1$AR, a 200 nM final concentration of $\alpha\beta_1$-MoDE-A was used in all cases, and inhibitors were added to the antibody/compound mixture before adding the mixture to cells. After the twelve hour incubation, cells were washed once with PBS and then incubated with trypsin at 37° C. for 5 minutes. Cells were then suspended in cold DMEM+10% FBS with 1 ug/ml propidium iodine and analyzed by flow cytometry.

Ternary Complex Assays

HepG2 cells were grown to greater than 90% confluency in a T75 plate. Cells were then washed with PBS and then removed from the culture plate by treatment with 1 mM EDTA/EGTA solution in PBS for 20 minutes at 37° C. The cells were then pelleted (7 minutes, 300×g), and resuspended in ice-cold assay medium (opti-MEM+0.1% BSA) to replenish calcium. The cells were pelleted and resuspended an additional 3 times. Cells were then aliquoted into a 96-well U bottom plate at approximately 35,000 cells per well. Pre-mixed solutions of $\alpha\beta_1$-MoDE-A or COR1-OH3 with anti-$\beta_1$AR were then added to cells (8-5000 nM final concentrations of $\alpha\beta_1$-MoDE-A or COR1-OH3 with 100 nM final concentration of anti-$\beta_1$AR) and incubated on ice for 30 minutes. The samples were then gently mixed via pipette and incubated on ice for an additional 30 minutes. Cells were then pelted (5 minutes, 300×g) and resuspended in assay media. This was repeated twice more, and cells were finally resuspended in assay media with 1 ug/ml propidium iodide. The cells were then analyzed by flow cytometry.

In Vitro Assay

Cells were grown in 24-well plates, and washed gently with PBS before adding antibody and D-MoDE-A. Compound (at 40 nM final concentration) and antibody (at 100 nM final concentration) where applicable were premixed and added to cells. At the given time point, cell culture media was collected and cells were washed 4× with PBS for 5 minutes each. Cells were then treated with PBS with 1×RIPA buffer (Millipore-Sigma, 20-188) with protease inhibitor tablets containing EDTA (Sigma, 11697498001) (50 µL per well). Cells were incubated on ice for 5 minutes, after which each well was thoroughly washed with pipette and collected. Lysates were briefly centrifuged before taking supernatant samples for gel analysis to avoid aspirating the cell pellet. 5 μL of each cell lysate was added per lane. For supernatants, 0.2 μL of the supernatant was added for each lane.

For western blots, samples were diluted into Laemeli buffer containing SDS but not β-mercaptoethanol. Samples were boiled for 2 minutes in PCR tubes using an S1000 thermal cycler. Samples were then loaded onto anyKd gels (Bio-rad, 4569033) and run at 120V using a BIORAD mini-protean tetra system with a BIORAD power pack. Gels were then transferred to 0.45 um Immobilon-P PVDF membranes (Immobilon, Cat. No. IPVH00010) using 300 mA for 1 hour at 4° C. in transfer buffer (20% MeOH, 25 mM tris base, 192 mM glycine). Membranes were then blocked with 0.2 μm-filtered 5% BSA in PBS for 1 hour. Anti-AF488 polyclonal antibody (Thermo, A-11094) diluted 1:10,000 into PBS containing 5% BSA was then added and the blots rocked gently for 1 hour. The membranes were then washed three times with PBS containing 0.2% Tween 20 (AmericanBio, Ref AB02038-00500) for 5 minutes each, then probed with HRP-conjugated goat α-rabbit antibody (1:10,000 in PBS containing 5% BSA, Abcam, ab205718). The membranes were gently rocked for 1 hour at room temperature, then washed 3 times with PBST for 5 minutes each and imaged. In the case of actin, we utilized an α-actin mouse antibody (Abcam, ab8226) followed by goat α-mouse HRP conjugate (Abcam, ab205719). Gels were imaged using a BIO-RAD ChemiDoc touch imaging system.

In Vivo Assay

In vivo experiments were performed under Yale University IACUC supervision following protocol entitled "preclinical evaluation of small molecule immunomodulators" (Protocol number 2017-11445). Experiments were performed in male nude mice purchased from Jackson Laboratory (NU/J, Stock No. 002019). Compounds were administered i.p. in a volume of 100 μL PBS. Approximately 25 μL of blood was collected at each time point by saphenous bleed. Antibody was administered as 40 μg in 100 μL i.p. Compounds were administered daily at the specified dose throughout the course of experiments. For data analysis, antibody levels were normalized to the recorded concentration of antibody observed in each mouse 24 hours after the i.p. administration.

ELISA to Measure Serum Levels of Anti-$\beta_1$AR Antibody

ELISA analysis of serum samples was performed using MaxiSorp 96 well plates (Thermo, 44-2404-21). For ELISAs to measure anti-$\beta_1$AR antibody in serum, plates were coated with 50 μL of α$\beta_1$-MoDE-A at 0.6 μM in PBS and incubated at 4° C. overnight. Coating solution was then removed, and the plates were blocked with 200 μL 2% BSA in PBS for 2 hours at room temperature, followed by washing three times with PBST (0.2% Tween). Serum samples were diluted 1:400 in 2% BSA in PBS. 100 μL of the diluted samples were added to the plate for 1 hour at RT. Plates were then washed with PBST (3 times), followed by addition of 100 μL goat anti-rat IgG-HRP conjugate (Ab 97057) diluted in 2% BSA in PBS (1:10,000). The plates were incubated for 1 hour at RT, then washed four times with PBST. The plates were then treated with 100 μL TMB (Thermo 34028) for 30 minutes in the dark followed by 50 μL 2 M sulfuric acid and analyzed for OD at 450 nm on a plate reader (BioTek Synergy 2). Sample concentrations were determined against a standard curve.

Microscopy Studies

Cells were grown in 8-well microscope cell culture containers (Thermo, 177402) treated with polylysine (Fisher Scientific, 343810001). For all experiments, D-MoDE-A was used at a final concentration of 40 nM, and antibody was used at a final concentration of 100 nM. At 12 hours, cell culture media was removed and cells were washed with PBS once before fixation with 3.5% formaldehyde PBS solution for 13 minutes. Cells were then washed with PBS, and permeabilized for 5 minutes with 0.5% triton X-100 in PBS. Cells were blocked with 0.2% tween in TBS (Tween 20, AmericanBio, Ref AB02038-00500) and 3% BSA (Sigma, A9418) for one hour at room temperature. Primary antibodies (EEA1, Abcam ab70521; Lamp2, Abcam ab25631) were diluted as suggested by the manufacturer into 0.2% TBST+ 3% BSA. After incubation for 1 hour in a humidified chamber protected from light, cells were washed 3× with PBST for 5 minutes each. Cells were then treated with Alexa Fluor 568-labeled secondary antibody (Abcam, ab175473) at 1:500 dilution. Cells were washed 3× with PBST for 5 minutes each, then treated with PBS containing Hoechst stain (final concentration 1 μg/mL), incubated at room temperature for at least 10 minutes, and imaged. Cells were visualized using a Zeiss Axio Observer Z1 inverted microscope using 63× magnification under oil. Image analysis was performed on ZEN2 (blue edition) version 2.0.0.0.

Mouse Monoclonal α-DNP Production

Antibodies were produced in U7.6 hybridoma cell lines donated by the Eshhar Lab at the Weizmann Institute. Purification and cell culture were carried out according to published methods (47). Cells were thawed and culture in 75 cm2 flasks (Corning, 353136) using high glucose DMEM containing pyruvate and L-glutamine (Invitrogen, 11995-065) supplemented with 15% Horse Serum (Invitrogen, 16050-114) and Pen strep (Invitrogen, 10378-016). Cells were passaged every 3 days until greater than 90% of the cells were viable. They were then transferred to CELLine1000 Bioreactors (VWR, 37003-008) through inoculation with approximately 75×106 cells. They were grown in the cell compartment in DMEM containing 15% IgG Depleted FBS (Invitrogen, 16250-078) and Pen/Strep. Nutrient compartment contained compartment media (DMEM supplemented with 5% horse serum and Pen/Strep). Cells were incubated for 5 days at 37° C. in a 5% CO2 atmosphere.

When cells reached 20-30×106 cells/mL, they were pelleted (300×g for 10 minutes) and the supernatant collected. Supernatant containing α-DNP IgG2a was clarified by filtration through a 0.22 micron sterile filter, then stored at −80° C. IgG was purified using 5 mL protein G spin columns (Thermo, 89961). Purity was confirmed using SDS-PAGE. Activity and isotype were confirmed using sandwich ELISA performed with DNP-modified BSA and an α-mouse IgG2a antibody (Novus Biologicals, 7511).

Mouse Polyclonal α-DNP Production

Mouse polyclonal serum was prepared by immunization of male C57BL/6 mice (Jackson Laboratory, stock no. 000664). Appropriately aged male mice (>6 weeks old) were chosen. DNP-KLH was suspended in sterile PBS to 2 mg/mL (2× solution). This was diluted 1:1 with Complete Freund's Adjuvant (from EMD Millipore) and vortexed to achieve a smooth suspension. For booster doses, Freund's incomplete adjuvant (iCFA) (from EMD Millipore) was used. For all doses, 100 μL was injected i.p. into mice. Two weeks post-immunization, mice were boosted by another injection of antigen. Following that, mice were boosted every week (up to five times) until the concertation of α-DNP was between 0.5 and 1.0 mg/mL, at which time serum was collected. Serum was pooled and injected into mice at a volume of 200 μL.

ELISA to Measure Serum Levels of α-DNP

ELISA analysis of serum samples was performed using MaxiSorp 96 well plates (Thermo, 44-2404-21). Plates were coated with 50 μL of BSA-DNP (Invitrogen, A23018) at 100 ug/mL in PBS and incubated at 4° C. overnight. Coating solution was then removed, and the plates were blocked with 2% BSA in PBS for 2 hours at room temperature, followed by washing twice with PBST (0.2% Tween). Serum samples were diluted in 2% BSA in PBS. For samples collected on days 1-4, serum was diluted 1:5,000. For day 5 and after, serum was diluted 1:1,000 to account for lower levels of circulating antibody present in serum. Diluted samples were added to the plate for 1 hour at RT. Plates were then washed with PBST (3 times), followed by addition of goat α-mouse IgG-HRP conjugate (Ab 97265) diluted in 2% BSA in PBS (1:10,000). The plates were incubated for 1 hour at RT, then washed three times with PBST. The plates were then treated with TMB (Thermo 34028) followed by 2 M H2SO4 and analyzed for OD at 450 nm on a plate reader (BioTek Synergy 2). Sample concentrations were determined against a standard curve.

AST/ALT Measurement

Figure 4:
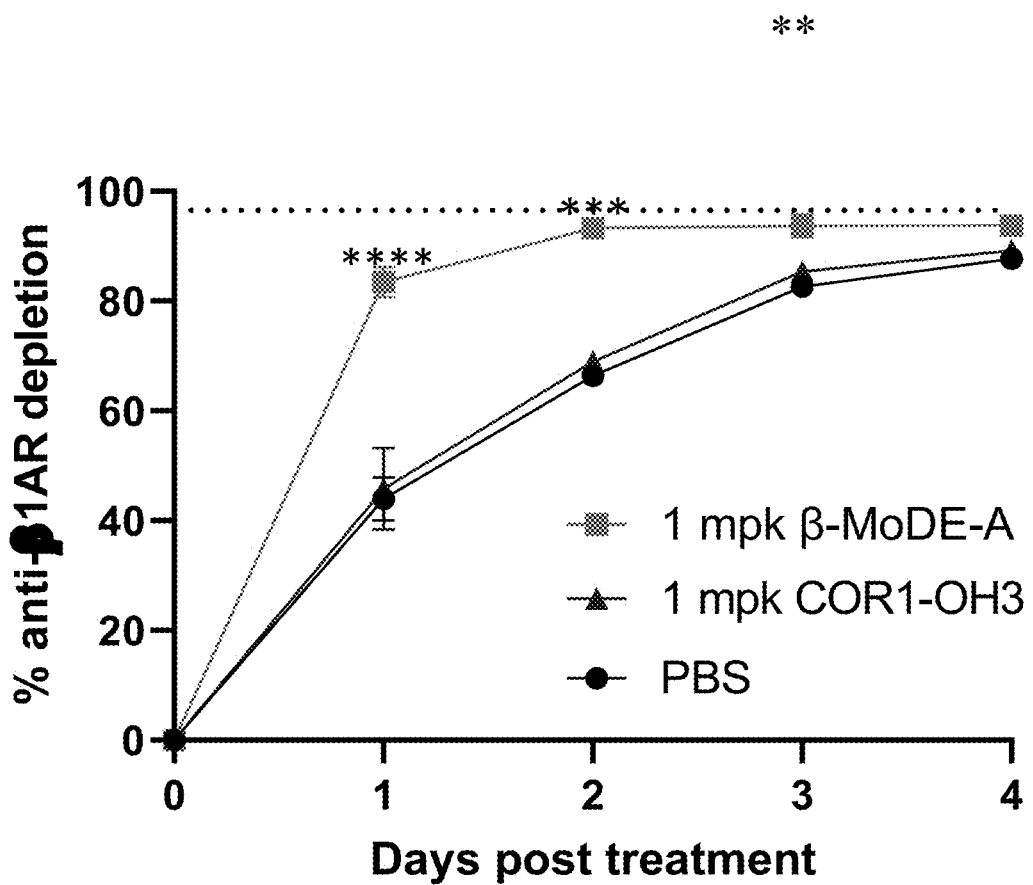
FIG. 4 shows in vivo depletion of target a$\beta_1$AR antibodies in the presence of a compound of Formula I as compared to a control compound (COR1-OH3). PBS=phosphate buffered saline; mpk=mg/kg.

AST and ALT levels were determined using pooled serum from mice from the study in FIG. 4C. Samples were submitted to the Mouse Metabolic Phenotyping Center at the Yale Diabetes Research Center.

Half-Life Determination

Half-life, AUC, and bioavailability were measured by Aurigene Discovery Technologies Ltd. Male nude mice were injected with 1 mpk dose i.p. in 200 μL 5% DMSO, 30% PEG300, and 65% water. Blood samples were collected (sub-mandibular) and the concentration of D-MoDE-A was measured by LC-MS/MS. Time points were 0, 5, 15, and 30 minutes, and 1, 2, 3, 6, 12, and 24 hours.

Synthetic Methods

General Chemistry Methods

Flash chromatography was performed on a CombiFlash NEXTGEN 300+ system by Teledyne ISCO running software version 5.0.62. Separation was accomplished on RediSep Rf High performance gold C18 columns (reverse phase) and RediSep Rf flash columns (normal phase). HPLC purification of compounds was performed using a Shimadzu chromatography system using a Waters SunFire C18 OBD Prep Column (10 mm×150 mm) and the LabSolutions Software Version 5.92. NMR analysis was performed on Agilent DD2 400 MHz and Agilent DD2 600 MHz NMR spectrometers. The 600 MHz instrument was equipped with a C[H] cold probe. HRMS analysis was performed on a Shimadzu 9030 Quadrupole Time-of-Flight LC-MS system following separation on a Shim-pack Scepter C18-120 1.9 μm (2.1×50 mm) reverse phase chromatography column. Separation was performed using a gradient of water to acetonitrile with the addition of 0.1% formic acid. Infrared (IR) spectra were collected using neat samples and recorded using a Thermo Nicolet 6700 equipped with a diamond ATR cell.

Select $v_{ma}$ are reported in $cm^{-1}$. Optical rotation was recorded on a Rudolph Autopol IV polarimeter. Chemicals were purchased from Sigma Aldrich, Fisher, and Carbosynth. Solvents were purchased from Fisher and Macron.

Synthetic Examples

Compound 1 (48)
2-(2-(2-hydroxyethoxy)ethoxy)ethyl 4-methylbenzenesulfonate

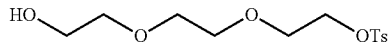 [SMILES: Cc1ccc(S(=O)(=O)OCCOCCOCCO)cc1]

Triethylene glycol (17.5 mL, 19.7 g, 131 mmol, 5 eq) was dissolved in dichloromethane (150 mL) and triethylamine (5.48 mL, 3.98 g, 1.5 eq) and cooled to 0° C. p-Toluenesulfonyl chloride (5.00 g, 26.2 mmol, 1.00 eq) was then added and the reaction mixture stirred at room temperature for 18 hours. The reaction was then diluted into dichloromethane and washed with water (3×) and brine (1×). The organic layer was dried over sodium sulfate and concentrated in vacuo to give compound 1 (6.89 g, 22.6 mmol) as a pale yellow oil in 85% yield, which was used without further purification. Spectra matched previously reported characterization data.

Compound 2 (48)
2-(2-(2-azidoethoxy)ethoxy)ethan-1-ol

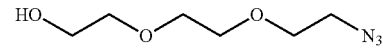

Tosylate 1 (2.00 g, 6.57 mmol) and sodium azide (0.470 g, 7.23 mmol, 1.1 eq) were dissolved in dimethylformamide (40 mL) and stirred overnight at 60° C. Volume was reduced by approx. half by rotary evaporation at 70° C., and the resulting mixture was diluted into water and extracted with ethyl acetate (2×). The combined organic layers were washed with brine (3×), dried over sodium sulfate, and evaporated to give azide 2 as a colorless oil (932 mg, 5.32 mmol) in 81% yield, which was used without further purification.

Compound 3 (49)

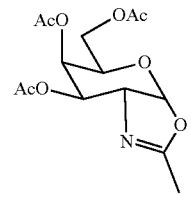

(5R,6R,7R,7aR)-5-(acetoxymethyl)-2-methyl-3a,6,7,7a-tetrahydro-5H-pyrano[3,2-d]oxazole-6,7-diyl diacetate D-Galactosamine pentaacetate (100 mg, 0.257 mmol) was dissolved in dichloroethane (1.0 mL) and stirred at room temperature under nitrogen atmosphere before the addition of trimethylsilyl trifluoromethanesulfonate (70.0 μL, 86.0 mg, 0.387 mmol, 1.50 eq). The reaction was stirred at 50° C. for 90 minutes, then allowed to cool to room temperature and stirred for a further 12 hours. The reaction was then poured into ice cold saturated aqueous sodium bicarbonate and extracted into dichloromethane. The organic layer was washed with water (2×) then dried over sodium sulfate and evaporated to give compound 3 (236 mg, 77.7 mmol, 92%) as a dark gum, which was used without further purification.

Compound 4 (50)
(2R,3R,4R,5R,6R)-5-acetamido-2-(acetoxymethyl)-6-(2-(2-(2-azidoethoxy)ethoxy)ethoxy)tetrahydro-2H-pyran-3,4-diyl diacetate

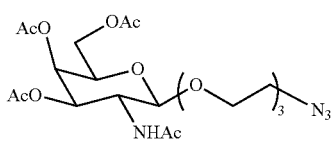

Compound 3 (200 mg, 0.607 mmol) and compound 2 (160 mg, 0.913 mmol, 1.50 eq) were dissolved in 1,2-dichloroethane (5 mL). 4 Å molecular sieves were then added, and the reaction stirred for 30 minutes. Trimethylsilyl trifluoromethanesulfonate (55.0 μL, 67.5 mg, 0.304 mmol, 0.5 eq) was then added to the mixture, and the reaction stirred overnight. The reaction was then diluted into dichloromethane, washed with 1 M sodium bicarbonate (1×) and water (1×), then dried over magnesium sulfate and concentrated. The crude oil was purified on silica gel (50-100% ethyl acetate in dichloromethane) to give compound 4 (245 mg, 0.486 mmol) as a white solid in 80.1% yield. Spectra matched previously reported characterization data.

Compound 5 (50)
(2R,3R,4R,5R,6R)-5-acetamido-2-(acetoxymethyl)-6-(2-(2-(2-aminoethoxy)ethoxy)ethoxy)tetrahydro-2H-pyran-3,4-diyl diacetate

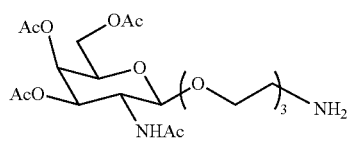

Compound 4 (1.80 g, 3.57 mmol) was dissolved in tetrahydrofuran (35 mL). Triphenylphosphine (1.40 g, 5.35 mmol, 1.5 eq) and water (257 μL, 14.28 mmol, 4 eq) were then added and the reaction stirred at room temperature under nitrogen for 36 hours. The solvent was removed and the crude product, a colorless oil, was used in the next step without further purification.

Compound 6 (51)
3,3'-((2-amino-2-((2-cyanoethoxy)methyl)propane-1,3-diyl)bis(oxy))dipropanenitrile

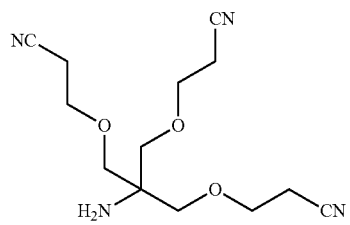 [SMILES: N#CCCOCC(N)(COCCC#N)COCCC#N]

Tris(hydroxymethyl)aminomethane (1.00 g, 8.25 mmol, 1.00 eq) was dissolved in dioxane (50 mL) and aqueous KOH (40% w/v, 1 mL) was added dropwise. Acrylonitrile (6.45 mL, 5.22 g, 25.2 mmol, 3.05 eq) was then added dropwise, and the reaction stirred overnight. Dioxane was removed in vacuo and the resulting aqueous solution was extracted with dichloromethane (3×). The combined organic layers were then washed with brine (1×), dried over sodium sulfate, and evaporated to give compound 6 as a colorless oil (1.12 g, 4.04 mmol) in 48.5% yield, which was used in further steps without purification. Spectra matched previously reported characterization data.

Compound 7 (52)
Dimethyl 3,3'-((2-amino-2-((3-methoxy-3-oxopropoxy)methyl)propane-1,3-diyl)bis(oxy))dipropionate

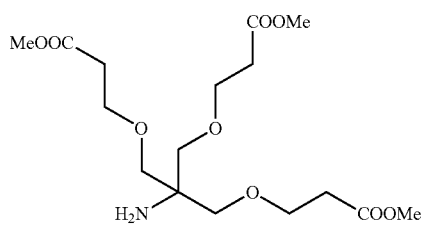 [SMILES: COC(=O)CCOCC(N)(COCCC(=O)OC)COCCC(=O)OC]

Compound 6 (710 mg, 2.50 mmol) was dissolved in methanol (30 mL) and sulfuric acid (2.8 mL) and heated at reflux for 24 hours. The solution was then cooled to 0° C., then neutralized with saturated sodium bicarbonate solution, and extracted into dichloromethane (3×). The organic layer was washed with brine, then dried over sodium sulfate and concentrated. The residue was purified on silica gel (0-10% methanol in dichloromethane) to give compound 7 as a colorless oil (656 mg, 1.73 mmol) in 69.0% yield. Spectra matched previously reported characterization data.

Compound 8
Methyl 8,8-bis((3-methoxy-3-oxopropoxy)methyl)-3,6-dioxo-1-phenyl-2,10-dioxa-4,7-diazatridecan-13-oate

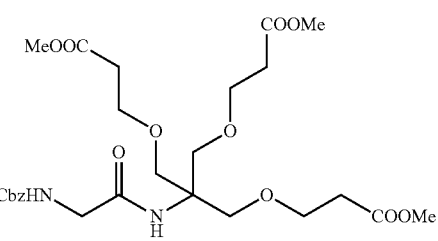

Compound 7 (723 mg, 1.90 mmol) was dissolved in acetonitrile (25 mL). 1-hydroxybenzotriazole hydrate (291 mg, 1.90 mmol, 1 eq), N-carbobenzyloxyglycine (397 mg, 1.90 mmol, 1.00 eq), and N,N'-dicyclohexylcarbodiimide (392 mg, 1.90 mmol, 1.00 eq) were then added, and the reaction stirred overnight. Acetonitrile was then evaporated, and the residue adsorbed onto silica and purified using a gradient of 0-75% ethyl acetate in hexanes. Compound 8 (866 mg, 1.52 mmol) was recovered as a colorless oil in 80% yield.

Compound 9
8,8-bis((2-carboxyethoxy)methyl)-3,6-dioxo-1-phenyl-2,10-dioxa-4,7-diazatridecan-13-oic acid

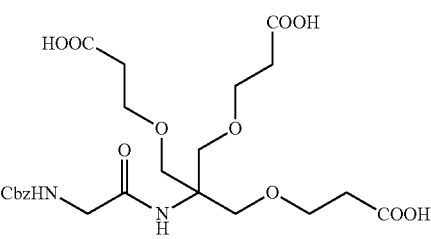 [SMILES: O=C(O)CCOCC(COCCC(=O)O)(COCCC(=O)O)NC(=O)CNC(=O)OCc1ccccc1]

Compound 8 (100 mg, 0.175 mmol) was dissolved in dioxane (2 mL) and aqueous NaOH (2 M, 2 mL). The reaction was stirred for 3 hours, then acidified to approximately pH 3 with 6 M hydrochloric acid and extracted twice into ethyl acetate. The organic fraction was washed with 1 M HCl, then dried over sodium sulfate and evaporated to give compound 9 as a white solid, which was used in further steps without purification.

Compound 10

Compound 11

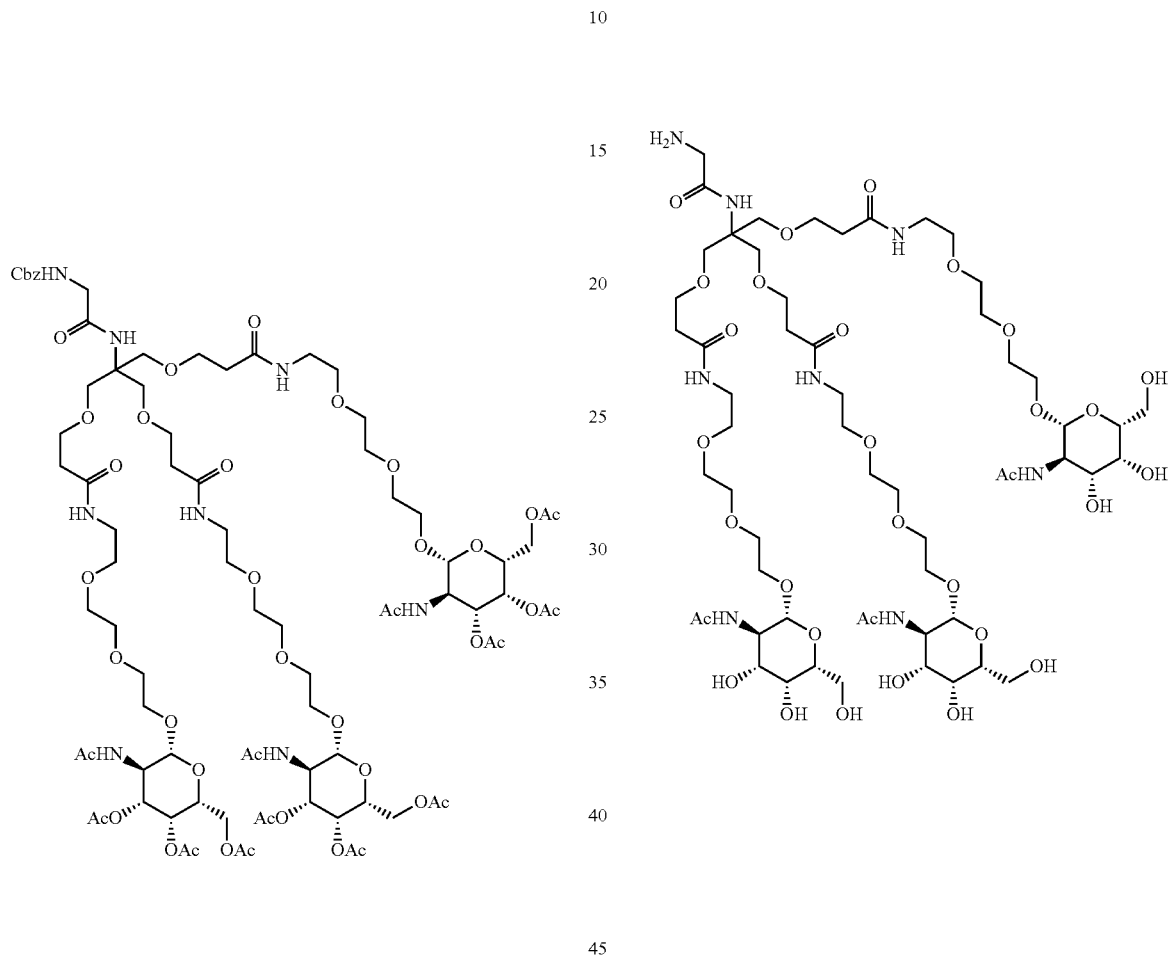

Compound 9 (372 mg, 0.704 mmol, 1 eq) was dissolved in dimethylformamide (40 mL) and diisopropylethylamine (981 µL, 728 mg, 5.63 mmol, 8.00 eq). N,N,N',N'-tetramethyl-O-(1H-benzotriazol-1-yl)uronium hexafluorophosphate (HBTU) (1.01 g, 2.67 mmol, 3.8 eq) was then added, and the reaction stirred for 10 minutes at room temperature before the addition of compound 5 (1.28 g, 2.67 mmol, 3.8 eq). The reaction was stirred for two hours, then diluted into dichloromethane and washed with aqueous solutions of phosphoric acid (1 M, 1×), sodium bicarbonate (1 M, 1×), and brine (1×). The organic layer was dried over sodium sulfate and evaporated onto silica. The residue was purified (0-20% methanol in dichloromethane) to give compound 10 (831 mg, 0.436 mmol) as a light brown solid in 62% yield.

Compound 10 (710 mg, 0.372 mmol) was dissolved in dry methanol (90 mL) and cooled to 0° C. under nitrogen. Palladium on carbon (71.0 mg, 10% w/w) was then added, and the reaction stirred under hydrogen atmosphere (1 atm) at 0° C. for 16 hours. Upon completion, the reaction was filtered through Celite and methanol was evaporated to give the intermediate amine (657 mg, 0.370 mmol) in 99.5% yield, which was used without further purification. The amine (441 mg, 0.248 mmol) was dissolved in methanol (15 mL) and cooled to 0° C. Sodium methoxide solution (400 µL, 5.4M in MeOH) was then added to effect removal of the O-acetyl groups, and the reaction was stirred for 30 minutes. Dowex 50WX8 was then added until the solution was weakly acidic. The resin was filtered and washed thoroughly with methanol. The combined methanol fractions were evaporated under reduced pressure to give compound 11 (274 mg, 0.196 mmol) as a colorless oil in 79.0% yield. Compound 11 was used in further steps without purification.

Compound 12 benzyl (1-hydroxy-15,15-bis(14-hydroxy-5-oxo-2,9,12-trioxa-6-azatetradecyl)-10,17-dioxo-3,6,13-trioxa-9,16-diazaoctadecan-18-yl)carbamate Compound 13

3,3'-((2-(2-aminoacetamido)-2-(14-hydroxy-5-oxo-2,9,12-trioxa-6-azatetradecyl)propane-1,3-diyl)bis(oxy))bis(N-(2-(2-(2-hydroxyethoxy)ethoxy)ethyl)propanamide)

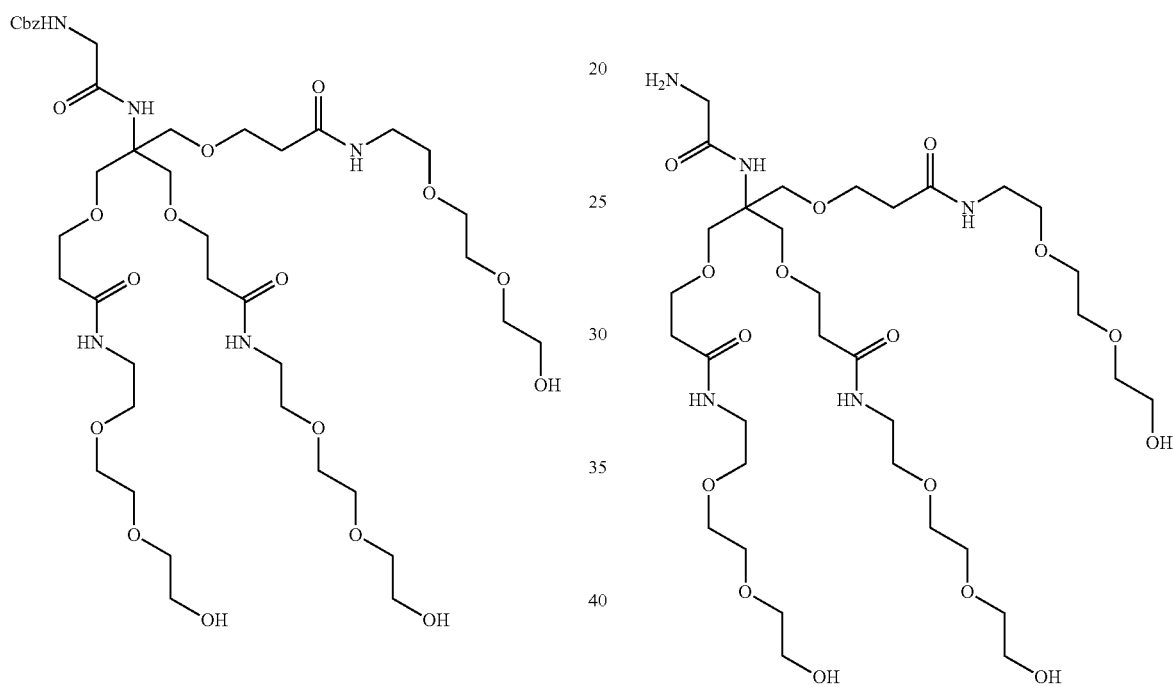

Compound 9 (302 mg, 0.572 mmol, 1 eq) was dissolved in dichloromethane (25 mL) and triethylamine (480 µL, 3.431 mmol, 6.00 eq). 1-Hydroxybenzotriazole hydrate (350 mg, 2.28 mmol, 4 eq) and 1-ethyl-3-(3-dimethylaminopropyl)carbodiimide (417 mg, 2.17 mmol, 3.80 eq) were then added, followed by 2-[2-(2-Aminoethoxy)ethoxy]ethanol (300 mg, 2.01 mmol, 3.80 eq). The reaction was then stirred overnight. The solvent was evaporated and the crude material was purified by reverse phase chromatography without workup using a gradient of 5-35% acetonitrile in water with the addition of 0.1% formic acid. Compound 12 was recovered in 65% yield as a colorless oil (345 mg, 0.372 mmol).

Compound 12 (345 mg, 0.374 mmol, 1.00 eq) was dissolved in methanol (15 mL). The solution was purged under a stream of nitrogen for five minutes. 10% Pd/C (5% w/w, 17.3 mg) was then added under a stream of nitrogen. The mixture was purged with hydrogen gas for 5 minutes and then stirred for 2 hours under a hydrogen atmosphere. The mixture was then filtered through a bed of Celite and the filtrate concentrated in vacuo to give compound 13 as a colorless oil in 96% yield (282 mg, 0.359 mmol). Compound 13 was used in further steps without purification.

Compound 14 (53)
ethyl 4-((2-chloroquinolin-6-yl)oxy)butanoate

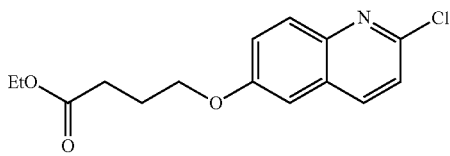 [SMILES: CCOC(=O)CCCOc1ccc2nc(Cl)ccc2c1]

2-Chloroquinolin-6-ol (1.00 g, 5.57 mmol) and potassium carbonate (1.53 g, 11.1 mmol, 2.0 eq) were dissolved in dimethylformamide (20 mL). Ethyl bromobutyrate (1.63 g, 1.2 mL, 8.35 mmol, 1.5 eq) was then added and the mixture stirred at 80° C. for 12 hours. The reaction was diluted into ethyl acetate and washed with water (2×) and brine (3×). The organic layer was dried over sodium sulfate and evaporated to give compound 14 as a pale yellow solid, which was used in the next step without further purification. Spectra matched previously reported characterization data.

Compound 15 (53)
ethyl 4-((2-((trimethylsilyl)ethynyl)quinolin-6-yl)oxy)butanoate

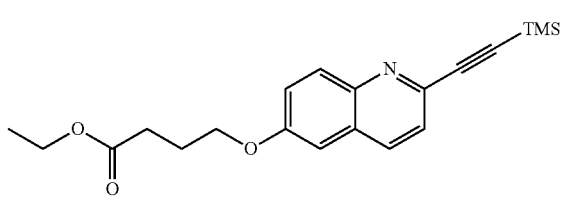 [SMILES: CCOC(=O)CCCOc1ccc2nc(C#C[Si](C)(C)C)ccc2c1]

Compound 14 (1.52 g, 5.17 mmol) was dissolved in tetrahydrofuran (20 mL) and triethylamine (2.88 mL, 20.7 mmol, 4 eq). Copper (I) iodide (49.0 mg, 0.258 mmol, 0.050 eq), Bis(triphenylphosphine)palladium(II) dichloride (181 mg, 0.258 mmol, 0.050 eq), and trimethylsilylacetylene (1.07 mL, 762 mg, 7.75 mmol, 1.50 eq) were then added and the reaction was stirred in a pressurized vessel at 65° C. for 16 hours. The reaction mixture was then cooled and filtered through Celite. The Celite was washed extensively with ethyl acetate, and the combined organic fractions were evaporated. The residue was purified on silica (0-50% ethyl acetate in hexanes) to give compound 15 in 81% yield (1.49 g, 4.19 mmol) as a pale yellow solid. Spectra matched previously reported characterization data.

Compound 16 (53)
ethyl 4-((2-ethynylquinolin-6-yl)oxy)butanoate

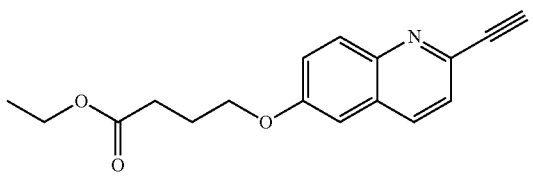 [SMILES: C#Cc1ccc2cc(OCCCC(=O)OCC)ccc2n1]

Compound 15 (1.57 g, 4.42 mmol) was dissolved in dichloromethane (45 mL) and tetrabutylammonium fluoride (5.30 mL, 1.00 M in THF, 5.30 mmol, 1.20 eq) was added dropwise. After 1 minute of stirring, 10% citric acid (50 mL) was added and the reaction stirred for 30 minutes. The organic phase was washed with water (1×), dried, and evaporated to give compound 16 as a pale yellow solid, which was used in the next step without further purification. Spectra matched previously reported characterization data.

Compound 17 (53)
ethyl 4-((2-(1-(3-fluoro-4-hydroxyphenyl)-1H-1,2,3-triazol-4-yl)quinolin-6-yl)oxy)butanoate

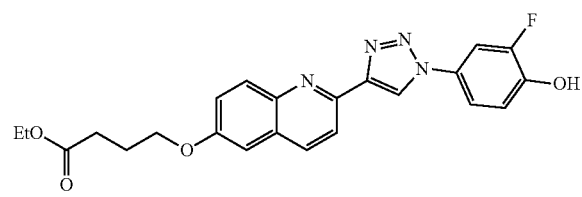 [SMILES: CCOC(=O)CCCOc1ccc2nc(-c3cn(-c4ccc(O)c(F)c4)nn3)ccc2c1]

2-Fluoro-4-iodophenol (126 mg, 0.529 mmol) and sodium azide (38 mg, 0.528 mmol, 1.0 eq) were dissolved in DMSO (2.5 mL) and stirred for 2 hours at 70° C. Compound 32 (150 mg, 0.529 mmol, 1 eq), trans-N,N'-dimethylcyclohexane-1,2-diamine (11 mg, 0.079 mmol, 0.15 eq), sodium ascorbate (10 mg, 0.053 mmol, 0.1 eq), copper (I) iodide (15 mg, 0.079 mmol, 0.15 eq), and $H_2O$ (2.5 mL) were then added, and the mixture stirred at 70° C. overnight. The reaction was diluted with ethyl acetate and washed with water (1×) and brine (1×). The organic layer was dried over sodium sulfate, evaporated, and purified on silica (0-100% ethyl acetate in dichloromethane) to give compound 17 as an off-white solid. Spectra matched previously reported characterization data.

Compound 18 (53)
4-((2-(1-(3-fluoro-4-hydroxyphenyl)-1H-1,2,3-triazol-4-yl)quinolin-6-yl)oxy)butanoic acid

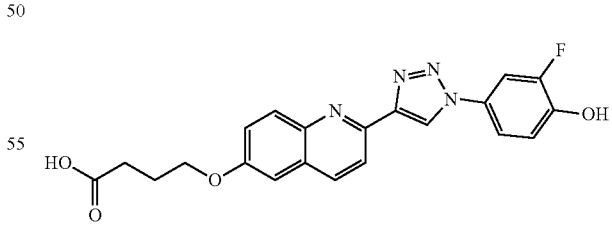

Compound 17 (90.0 mg, 0.206 mmol) was dissolved in dioxane (6.00 mL) and 2 M NaOH (3.00 mL). The reaction was stirred for 2.5 hours at room temperature, at which time the reaction was diluted with water and the pH adjusted to 3 with 1 M HCl. The mixture was cooled to 4° C. and filtered to give compound 18 as a brown powder, which was used without further purification.

Compound 19 (54)
2-(2-(2-(2-hydroxyethoxy)ethoxy)ethoxy)ethyl 4-methylbenzenesulfonate

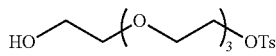

Tetraethylene glycol (50.0 g, 258 mmol) was dissolved in tetrahydrofuran (10 mL), cooled to 0° C., and stirred. Sodium hydroxide (1.68 g, 41.3 mmol, 1.60 eq) in water (10 mL) was then added, followed by the dropwise addition of p-toluenesulfonyl chloride (5.00 g, 25.8 mmol, 1.00 eq) in tetrahydrofuran (3 mL). The reaction mixture was stirred at 0° C. for 4 hours, then diluted into dichloromethane. The organic layer was washed with ice-cold water (2×) and brine (1×), then dried over sodium sulfate to give compound 19 (8.84 g, 25.4 mmol, 99.0% yield) as a pale yellow oil, which was used in further steps without purification.

Compound 20 (54)
2-(2-(2-(2-azidoethoxy)ethoxy)ethoxy)ethan-1-ol

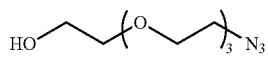

Compound 19 (8.84 g, 25.4 mmol) was dissolved in 100% ethanol (200 mL) and sodium azide (4.128 g, 63.5 mmol, 2.50 eq) was added. The reaction was heated to reflux for 16 hours, then cooled to room temperature before the addition of water (150 mL). Ethanol was then evaporated under reduced pressure and the aqueous layer extracted into ethyl acetate (2×). The organic layer was washed with water (1×) and brine (1×), dried over sodium sulfate, and evaporated to give compound 20 (4.82 g, 22.1 mmol) as a yellow oil in 87.0% yield. Spectra matched previously reported characterization data.

Compound 21 (55)
2-(2-(2-(2-azidoethoxy)ethoxy)ethoxy)acetic acid

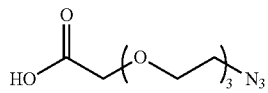

Ice-cold Jones reagent was prepared separately by mixing chromium trioxide (1.37 g, 13.68 mmol, 3.00 eq), $H_2SO_4$ (2.38 mL), and water (26.2 mL) at 0° C. Jones reagent was then added dropwise to an ice-cold solution of compound 20 (1.00 g, 4.56 mmol, 1 eq) in acetone (20 mL). The reaction was then warmed to room temperature and stirred for 16 hours. Excess Jones reagent was quenched by the addition of isopropanol (30 mL) and the reaction concentrated. The aqueous residue was then extracted with dichloromethane (4×). The organic layers were combined, dried over sodium sulfate, and concentrated to give compound 21 (851 mg, 3.65 mmol) as a colorless oil in 80% yield, which was used in further steps without purification.

Compound 22 (56)
2-(2-(2-(2-aminoethoxy)ethoxy)ethoxy)acetic acid

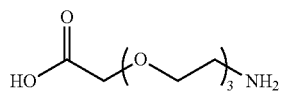

Compound 21 (2.4 g, 10.3 mmol) was dissolved in methanol and the atmosphere flushed with $N_2$. Palladium on carbon (240 mg, 10% w/w) was added, and the flask purged again with nitrogen. The flask was then purged with $H_2$ gas and stirred under $H_2$ atmosphere for 16 hours. The reaction then filtered through celite and concentrated to give compound 22 (2.13 g, 10.3 mmol) as a colorless oil in quantitative yield. Compound 22 was used in further steps without purification.

Compound 23
2-(2-(2-(2-((2,4-dinitrophenyl)amino)ethoxy)ethoxy)ethoxy)acetic acid

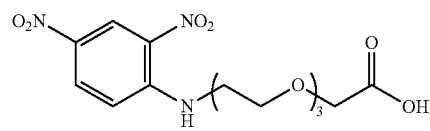

1-Chloro-2,4-dinitrobenzene (52.8 mg, 0.261 mmol, 1.00 eq), compound 22 (75.5 mg, 0.365 mmol, 1.40 eq), and sodium bicarbonate (65.7 mg, 0.782 mmol, 3.00 eq) were dissolved in water (2 mL) in a round bottom flask. The flask was then equipped with a reflux condenser and the mixture stirred at 95° C. for 16 hours. The reaction was then cooled and diluted into saturated sodium bicarbonate solution (10 mL), then washed with dichloromethane. The aqueous solution was then treated with concentrated hydrochloric acid until the pH of the solution was below 2. The aqueous layer was then extracted twice with dichloromethane. The combined organic layers were dried over sodium sulfate and concentrated to give compound 23 (86.8 mg, 0.232 mmol) as a bright yellow oil in 89% yield, which was used without further purification.

Compound 24 (D-MoDE-A)

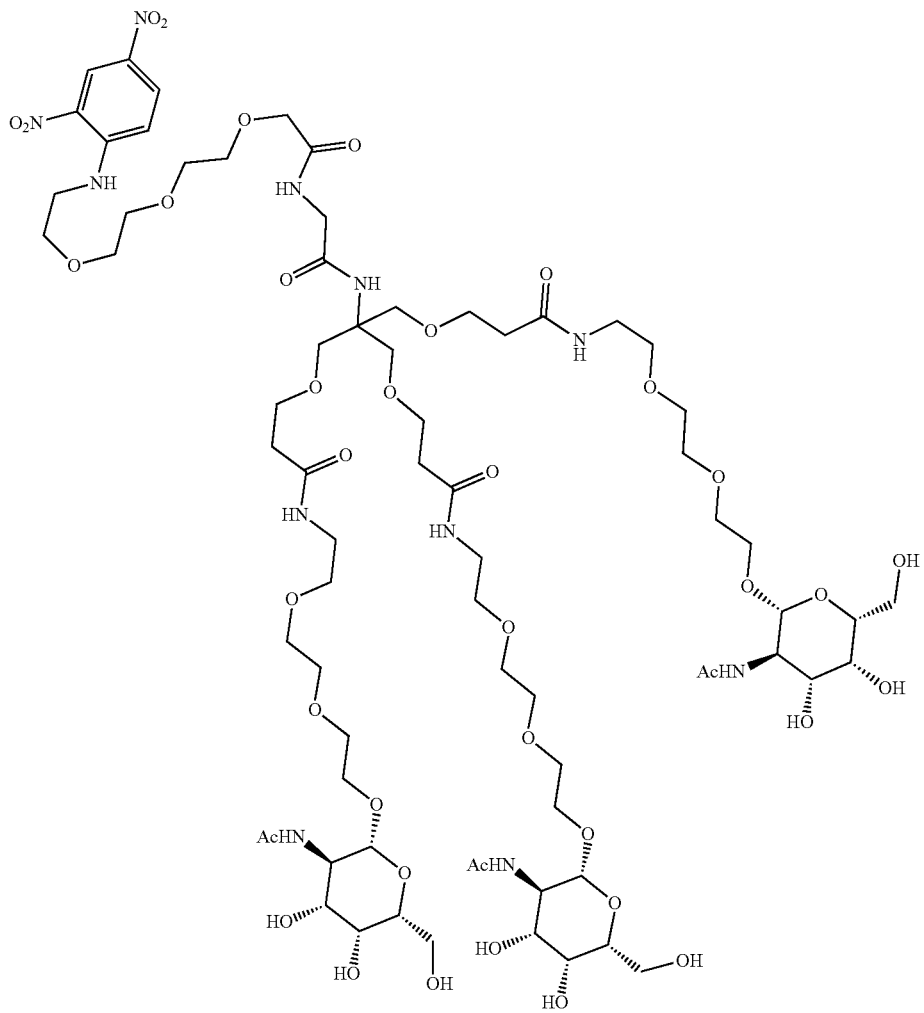 [SMILES: CC(=O)N[C@H]1[C@H](OCCOCCOCCNC(=O)CCOCC(COCCC(=O)NCCOCCOCCO[C@@H]2O[C@H](CO)[C@H](O)[C@H](O)[C@H]2NC(C)=O)(COCCC(=O)NCCOCCOCCO[C@@H]2O[C@H](CO)[C@H](O)[C@H](O)[C@H]2NC(C)=O)NC(=O)CNC(=O)COCCOCCOCCNc2ccc([N+](=O)[O-])cc2[N+](=O)[O-])O[C@H](CO)[C@H](O)[C@@H]1O]

Compound 23 (75.1 mg, 0.201 mmol, 1.5 eq) was dissolved in dichloromethane (7 mL) and diisopropylethylamine (26 mg, 0.201 mmol, 1.5 eq). 1-hydroxybenzotriazole hydrate (34.9 mg, 0.2278 mmol, 1.7 eq) and 1-Ethyl-3-(3-dimethylaminopropyl)carbodiimide (41.0 mg, 0.214 mmol, 1.6 eq) were then added and stirred for 10 minutes. Cbz-deprotected amine 9-OAc (238 mg, 0.134 mmol, 1 eq) was added, then the reaction mixture stirred overnight. Mixture was diluted into dichloromethane (50 mL) and washed with water (2×) and brine (1×). The organic layer was dried over sodium sulfate and concentrated. The residue was dissolved in methanol (3.5 mL) and chilled to 0° C. Sodium methoxide solution (5.4 M in methanol, 292 µL) was then added, and the reaction stirred at 0° C. for 30 minutes. It was then neutralized with Dowex 50WX8. The reaction was filtered and concentrated. The residue was directly purified on HPLC (0-30% acetonitrile in water, +0.1% formic acid) to give compound 24 as a bright yellow powder in 18.6% yield (0.0249 mmol, 43.7 mg).

Compound 25 (M-MoDE-A)

Compound 26 (DNP-OH3)

3,3'-((2-(14-((2,4-dinitrophenyl)amino)-4-oxo-6,9,12-tri-oxa-3-azatetradecanamido)-2-(14-hydroxy-5-oxo-2,9,12-trioxa-6-azatetradecyl)propane-1,3-diyl)bis(oxy))bis(N-(2-(2-(2-hydroxyethoxy)ethoxy)ethyl)propanamide)

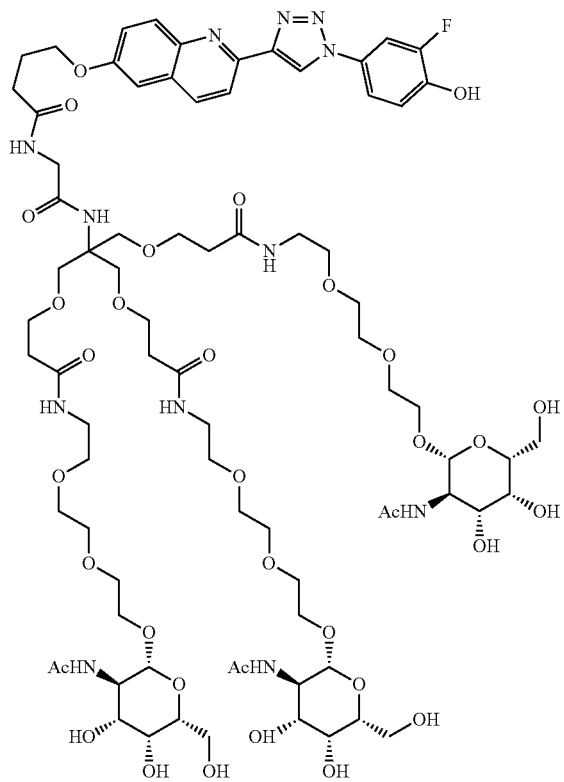 [SMILES: CC(=O)N[C@H]1[C@H](OCCOCCOCCNC(=O)CCOCC(COCCC(=O)NCCOCCOCCO[C@@H]2O[C@H](CO)[C@H](O)[C@H](O)[C@H]2NC(C)=O)(COCCC(=O)NCCOCCOCCO[C@@H]2O[C@H](CO)[C@H](O)[C@H](O)[C@H]2NC(C)=O)NC(=O)CNC(=O)CCCOc2ccc3nc(-c4cn(-c5ccc(O)c(F)c5)nn4)ccc3c2)O[C@H](CO)[C@H](O)[C@@H]1O]

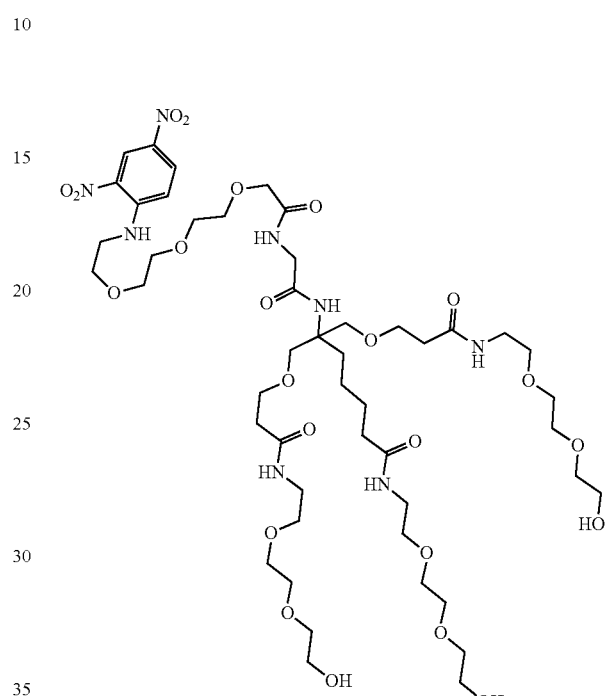

Compound 18 (23.5 mg, 0.0575 mmol, 1.1 eq) and (1-[Bis(dimethylamino)methylene]-1H-1,2,3-triazolo[4,5-b]pyridinium 3-oxide hexafluorophosphate (HATU) (20.0 mg, 0.0522 mmol, 1 eq) were dissolved in dry dimethylformamide (5 mL) and diisopropylethylamine (23.3 µL, 16.9 mg, 0.131 mmol, 2.5 eq) and stirred for 10 minutes at room temperature. Compound 11 (73.0 mg, 0.0522 mmol) was then added, and the reaction stirred for 30 minutes. The mixture was loaded directly onto HPLC and purified (20-30% acetonitrile in water, +0.3% trifluoroacetic acid) to give compound 25 (12 mg, 0.0067 mmol) as an off-white powder in 12.8% yield.

Compound 13 (234 mg, 0.297 mmol, 1 eq) was dissolved in dimethylformamide (5 mL) and triethylamine (83 µL, 0.594 mmol, 2 eq). Compound 23 (110.9 mg, 0.297 mmol, 1 eq) and 1-Hydroxybenzotriazole hydrate (59 mg, 0.386 mmol, 1.3 eq) were then added, followed by 1-ethyl-3-(3-dimethylaminopropyl)carbodiimide (68.3 mg, 0.356 mmol, 1.2 eq). The reaction was stirred overnight, then evaporated under a stream of nitrogen. Product was purified directly via reverse phase HPLC (0-30% acetonitrile in water +0.1% formic acid) to give compound 26 (178 mg, 0.155 mmol) as a bright yellow powder in 52.3% yield.

General Synthetic POrocedures for COR1-GN3 Compounds

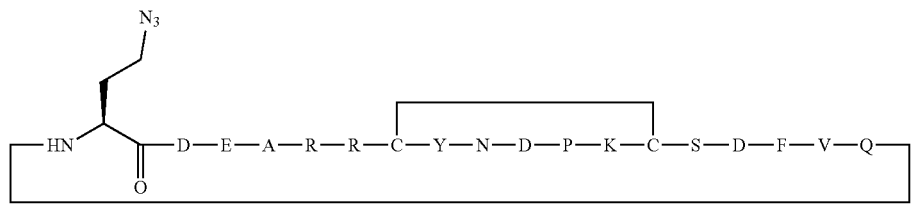

The backbone of N₃COR1 ((Azidohomoalinine)-DE-ARRCYNDPKCSDFVQ) was synthesized following standard Fmoc-based SPPS conditions. The peptide was cleaved from resin using 20% HFIP in DCM (1×1 h, 1×30 min) and the solvent was evaporated under N₂ gas. The crude material was dissolved in DMF containing HATU (3 eq), HOAt (4 eq), and DIEA (6 eq) and stirred overnight at RT. The DMF was then removed by rotevap and the material was further dried under high vac for 1 h. The peptide was then deblocked with TFA/TIPS/thioanisole/water (89:3:3:5 v/v) for 2 h and the solvent was evaporated under N₂. The peptide was then ether precipitated (2×50 ml) using ice cold ether and centrifuged (2500 rcf×2.5 min). The ether was removed and the resulting pellet was dissolved in H₂O/MeCN/DMSO (1:1:1 v/v) and stirred at RT for 48 hours. The crude peptide was then purified by HPLC (MeCN/H₂O+0.1% TFA, 0-80% MeCN), yielding azido-COR1 100.

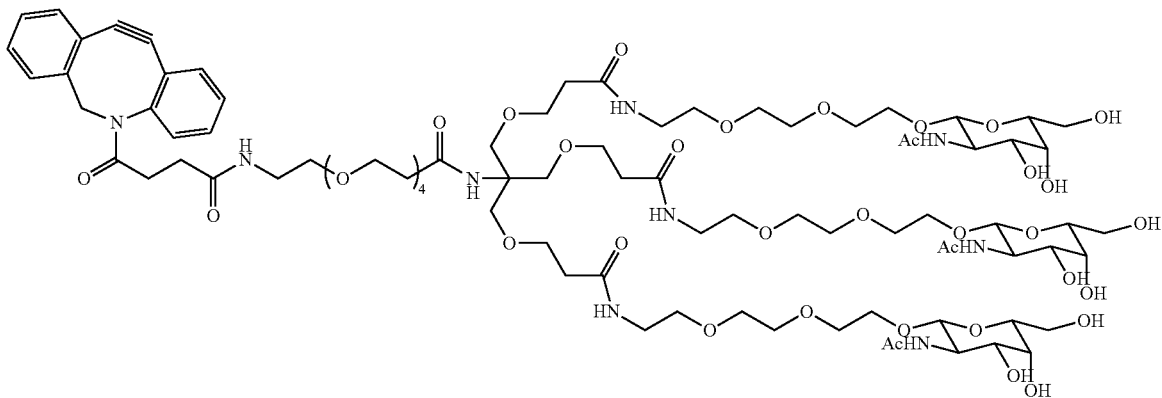

Compound 11 (NH₂GN3) was dissolved in DMF, followed by addition of DBCO-PEG₄-NHS ester (CAS #1427004-19-0) (1.5 eq) and DIEA (5 eq). The reaction was stirred overnight at RT, diluted in H₂O+0.1% TFA, and purified by HPLC (MeCN/H₂O+0.1% TFA, 0-80% MeCN), yielding 101.

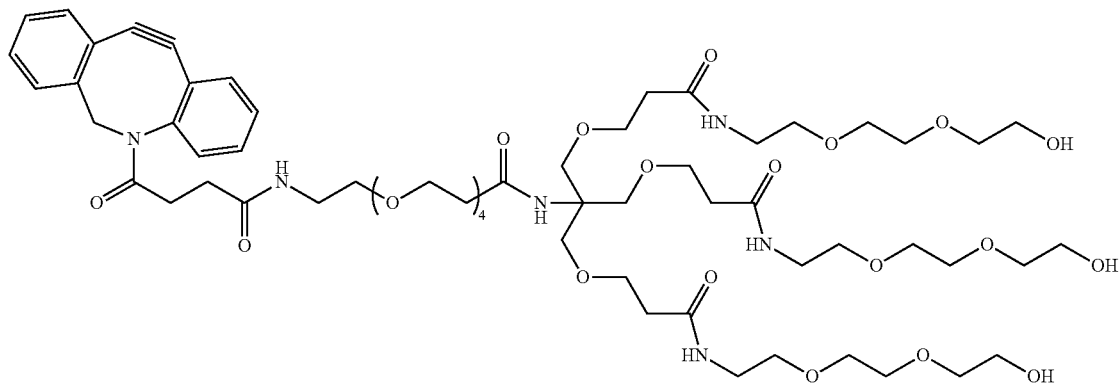

Compound 12 (NH₂OH3) was dissolved in DMF, followed by addition of DBCO-PEG₄-NHS ester (CAS #1427004-19-0) (1.5 eq) and DIEA (5 eq). The reaction was stirred overnight at RT, diluted in H₂O+0.1% TFA, and purified by HPLC (MeCN/H₂O+0.1% TFA, 0-80% MeCN), yielding 102.

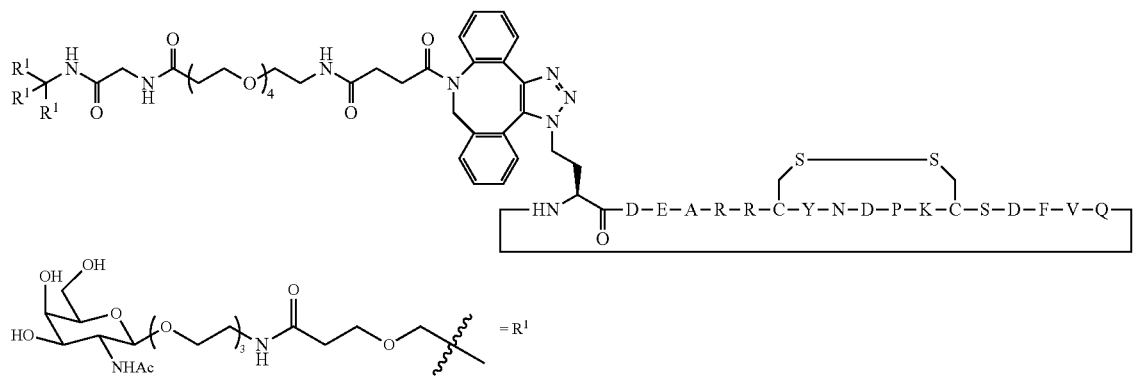

Compound 100 (1 eq) and compound 101 (1.5 eq) were dissolved in H₂O/MeCN (1:1 v/v) and stirred overnight at room temperature. The crude mixture was then purified by HPLC (MeCN/H₂O+0.1% TFA, 0-80% MeCN), to yield β-MoDE-A.

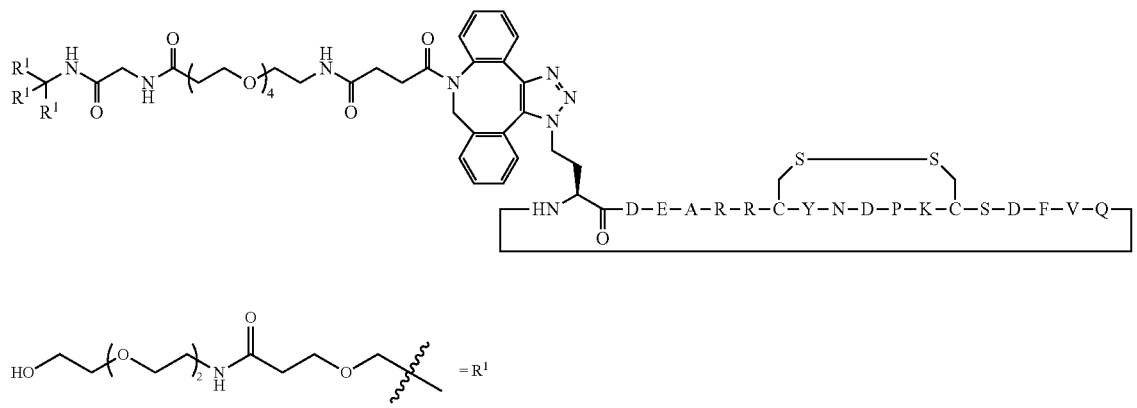

Compound 100 (1 eq) and compound 102 (1.5 eq) were dissolved in H₂O/MeCN (1:1 v/v) and stirred overnight at room temperature. The crude mixture was then purified by HPLC (MeCN/H₂O+0.1% TFA, 0-80% MeCN), to yield COR1-OH3.

The terms and expressions employed herein are used as terms of description and not of limitation, and there is no intention in the use of such terms and expressions of excluding any equivalents of the features shown and described or portions thereof, but it is recognized that various modifications are possible within the scope of the embodiments of the present application. Thus, it should be understood that although the present application describes specific embodiments and optional features, modification and variation of the compositions, methods, and concepts herein disclosed may be resorted to by those of ordinary skill in the art, and that such modifications and variations are considered to be within the scope of embodiments of the present application.

Enumerated Embodiments

The following enumerated embodiments are provided, the numbering of which is not to be construed as designating levels of importance:

Embodiment 1 provides a compound of Formula Ia, or a pharmaceutically acceptable salt thereof, having the structure:

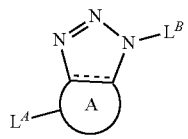

Formula Ia, wherein:

≡≡≡≡≡ is a carbon-carbon single or double bond;

A is a $C_{6-18}$ aryl, $C_{6-18}$ heterocyclyl, $C_{6-18}$ biaryl, or $C_{6-18}$ heterobiaryl, each of which is optionally substituted by 1-6 substituents selected from the group consisting of F, Cl, Br, I, ORG, OC(O)N(RG)$_2$, CN, NO, NO$_2$, ONO$_2$, CF$_3$, OCF$_3$, RG, N(RG)$_2$, SRG, SORG, SO$_2$RG, SO$_2$N(RG)$_2$, and SO$_3$RG;

$L^A$ is an ASGPR binding moiety with the structure

[structure: ⸺(XG)$_n$⸺C(=O)⸺NH⸺CH$_2$⸺C(=O)⸺NH⸺C(RG$^{1'}$)(RG$^1$)(RG$^1$)]

$L^B$ is an anti-b$_1$AR binding moiety with the structure

[structure: ⸺(CH$_2$)$_m$⸺CH(NH)⸺C(=O)⸺AA cyclic]

AA is an amino acid sequence at least 80% homologous to SEQ ID NO: 1;

RG$^{1'}$ is

[structure: AG⸺O⸺CH$_2$⸺(ZG)$_p$⸺O⸺]

each occurrence of R$^1$ is independently hydrogen or

[structure: AG⸺O⸺CH$_2$⸺(ZG)$_p$⸺O⸺]

AG is an aminosaccharide;

each occurrence of RG is independently H, optionally substituted $C_{1-10}$ alkyl, optionally substituted $C_{3-10}$ cycloalkyl, optionally substituted $C_{6-18}$ aryl, or optionally substituted $C_{5-18}$ heteroaryl;

each occurrence of XG is independently selected from the group consisting of —CH$_2$—, —C(=O)—, —NH—, and —O—;

each occurrence of ZG is independently selected from the group consisting of —CH$_2$—, —C(=O)—, —NH—, and —O—;

m is an integer from 2 to 10;

n is an integer from 1 to 100; and p is an integer from 1 to 50.

Embodiment 2 provides the compound of embodiment 1, wherein AG has the structure:

[structure: aminosaccharide with OH, OH, HO, and NRG$^3$RG$^2$ substituents]

wherein RG$^2$ and RG$^3$ are each independently selected from the group consisting of hydrogen and —C(=O)R, which is optionally substituted by 1-5 groups selected from the group consisting of halogen, optionally substituted $C_{1-10}$ alkyl, optionally substituted $C_{1-10}$ alkoxy, optionally substituted $C_{1-10}$ aminoalkyl, and combinations thereof, or RG$^2$ and RG$^3$ taken together with the nitrogen atom to which they are attached, form a C5 heterocycle that is optionally substituted by 1-5 substituents selected from the group consisting of optionally substituted $C_{1-10}$ alkyl, optionally substituted $C_{1-10}$ alkoxy, optionally substituted $C_{1-10}$ aminoalkyl, optionally substituted $C_{6-10}$ aryl, optionally substituted $C_{5-10}$ heteroaryl, halogen, and combinations thereof.

Embodiment 3 the compound of any one of embodiments 1-2, wherein RG$^2$ is hydrogen and RG$^3$ is C(=O)CH$_3$.

Embodiment 4 the compound of any one of embodiments 1-3, wherein each occurrence of (ZG)$_p$ independently has the structure:

[structure: ⸺H$_2$C⸺(O⸺CH$_2$CH$_2$)$_2$⸺NH⸺C(=O)⸺]

Embodiment 5 the compound of any one of embodiments 1-14, wherein (XG)$_n$ is selected from the group consisting of —O(CH$_2$)$_3$—, —NH—(CH$_2$CH$_2$O)$_3$—CH$_2$—, and =N*(C=O)(CH$_2$)$_2$C(=O)NHCH$_2$CH$_2$—(OCH$_2$CH$_2$)$_4$—, wherein =N* is a ring nitrogen in A.

Embodiment 6 the compound of any one of embodiments 1-5, wherein AA is a (6,12) cyclic peptide.

Embodiment 7 the compound of any one of embodiments 1-6, wherein AA is at least 95% homologous to SEQ ID NO:1.

Embodiment 8 the compound of any one of embodiments 1-7, wherein AA is an amino acid sequence of SEQ ID NO: 1.

Embodiment 9 the compound of any one of embodiments 1-8, having the structure

[structure: dibenzoazacyclooctyne-triazole with $L^A$ and $L^B$ substituents]

Embodiment 10 provides a method of preventing, treating, and/or ameliorating heart failure in a subject, the method comprising administering to the subject a composition comprising at least one pharmaceutically acceptable carrier and a therapeutically effective amount of the compound of any of embodiments 1-9.

Embodiment 11 the method of embodiment 10, wherein the heart failure is dilated cardiomyopathy (DCM).

Embodiment 12 the method of any one of embodiments 10-11, wherein the composition is administered by a route selected from the group consisting of oral, transdermal, transmucosal, (intra)nasal, (trans)rectal, intravesical, intrapulmonary, intraduodenal, intragastrical, intrathecal, subcutaneous, intramuscular, intradermal, intra-arterial, intravenous, intrabronchial, inhalation, and topical.

Embodiment 13 the method of any one of embodiments 10-12, wherein the composition is administered intravenously.

Embodiment 14 the method of any one of embodiments 10-13, wherein the composition is administered in a dose of about 0.01 mg/kg to about 20 mg/kg.

Embodiment 15 the method of any one of embodiments 10-14, wherein the subject is a mammal.

Embodiment 16 the method of any one of embodiments 10-15, wherein the subject is human.

What is claimed is:

1. A compound of Formula Ia, or a pharmaceutically acceptable salt thereof, having the structure:

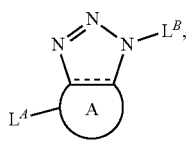

(Formula Ia)

wherein:

- ----- is a carbon-carbon single or double bond;
- A is $C_{6-18}$ aryl, $C_{6-18}$ heterocyclyl, $C_{6-18}$ biaryl, or $C_{6-18}$ heterobiaryl, wherein each of $C_{6-18}$ aryl, $C_{6-18}$ heterocyclyl, $C_{6-18}$ biaryl, and $C_{6-18}$ heterobiaryl is independently optionally substituted by 1-6 substituents selected from the group consisting of F, Cl, Br, I, O(RG), OC(O)N(RG)$_2$, CN, NO, NO$_2$, ONO$_2$, CF$_3$, OCF$_3$, (RG), N(RG)$_2$, S(RG), SO(RG), SO$_2$(RG), SO$_2$N(RG)$_2$, and SO$_3$(RG);
- $L^A$ is an asialoglycoprotein receptor (ASGPR) binding moiety with the structure

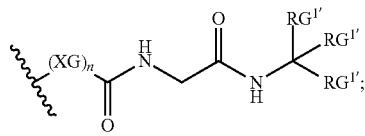

- $L^B$ is an anti-$\beta_1$AR binding moiety with the structure

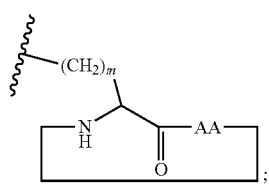

- AA is an amino acid sequence at least 80% homologous to SEQ ID NO:1;
- each occurrence of $RG^{1'}$ is independently

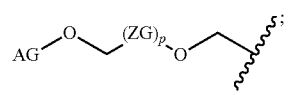

each occurrence of $RG^1$ is independently H or

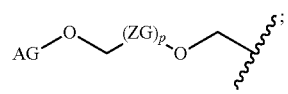

each occurrence of ZG is:

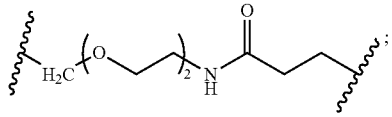

AG is

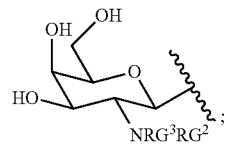

- $RG^2$ is H;
- $RG^3$ is C(=O)CH$_3$;
- each occurrence of RG is independently H, unsubstituted or substituted $C_{1-10}$ alkyl, unsubstituted or substituted $C_{3-10}$ cycloalkyl, unsubstituted or substituted $C_{6-18}$ aryl, or unsubstituted or substituted $C_{5-18}$ heteroaryl;
- each occurrence of XG is independently selected from the group consisting of one or more of —CH$_2$—, —C(=O)—, —NH—, and —O—;
- m is 2, 3, 4, 5, 6, 7, 8, 9, or 10;
- n is 1, 2, 3, 4, 5, 6, 7, 8, 9, 10, 11, 12, 13, 14, 15, 16, 17, 18, 19, 20; and
- p is 1, 2, 3, or 4.

2. The compound of claim 1, wherein (XG)$_n$ is selected from the group consisting of —O(CH$_2$)$_3$—, —NH—

$(CH_2CH_2O)_3$—$CH_2$—, and *—$C(=O)(CH_2)_2C(=O)$NHCH_2CH_2—$(OCH_2CH_2)_4$—, wherein the bond marked with * is to ring A.

3. The compound of claim 1, wherein AA is a (6,12) cyclic peptide in which the cysteine residues at positions 6 and 12 in AA form a disulfide bond.

4. The compound of claim 3, wherein AA is at least 95% homologous to SEQ ID NO:1.

5. The compound of claim 3, wherein AA is an amino acid sequence of SEQ ID NO:1.

6. The compound of claim 1, wherein the compound has the structure

7. A method of ameliorating heart failure in a subject in need thereof, the method comprising administering to the subject a therapeutically effective amount of a compound of Formula Ia (Formula Ia)

wherein:
   ===== is a carbon-carbon single or double bond;
   A is $C_{6-18}$ aryl, $C_{6-18}$ heterocyclyl, $C_{6-18}$ biaryl, or $C_{6-18}$ heterobiaryl, wherein each of $C_{6-18}$ aryl, $C_{6-18}$ heterocyclyl, $C_{6-18}$ biaryl, and $C_{6-18}$ heterobiaryl is independently optionally substituted by 1-6 substituents selected from the group consisting of F, Cl, Br, I, O(RG), OC(O)N(RG)$_2$, CN, NO, NO$_2$, ONO$_2$, CF$_3$, OCF$_3$, (RG), N(RG)$_2$, S(RG), SO(RG), SO$_2$(RG), SO$_2$N(RG)$_2$, and SO$_3$(RG);
   $L^A$ is an asialoglycoprotein receptor (ASGPR) binding moiety with the structure $L^B$ is an anti-$\beta_1$AR binding moiety with the structure AA is an amino acid sequence at least 80% homologous to SEQ ID NO:1;
each occurrence of $RG^{1'}$ is independently each occurrence of $RG^1$ is independently H or each occurrence of ZG is:

AG is $RG^2$ is H;
$RG^3$ is C(=O)CH$_3$;
each occurrence of RG is independently H, unsubstituted or substituted $C_{1-10}$ alkyl, unsubstituted or substituted $C_{3-10}$ cycloalkyl, unsubstituted or substituted $C_{6-18}$ aryl, or unsubstituted or substituted $C_{5-18}$ heteroaryl;
each occurrence of XG is independently selected from the group consisting of one or more of —CH$_2$—, —C(=O)—, —NH—, and —O—;
m is 2, 3, 4, 5, 6, 7, 8, 9, or 10;
n is 1, 2, 3, 4, 5, 6, 7, 8, 9, 10, 11, 12, 13, 14, 15, 16, 17, 18, 19, or 20; and
p is 1, 2, 3, or 4.

8. The method of claim 7, wherein the heart failure is dilated cardiomyopathy (DCM).

9. The method of claim 7, wherein the compound is administered by a route selected from the group consisting of oral, transdermal, transmucosal, (intra) nasal, (trans) rectal, intravesical, intrapulmonary, intraduodenal, intragastrical, intrathecal, subcutaneous, intramuscular, intradermal, intra-arterial, intravenous, intrabronchial, inhalation, and topical.

10. The method of claim 9, wherein the compound is administered intravenously.

11. The method of claim 7, wherein the compound is administered in a dose of about 0.01 mg/kg to about 20 mg/kg.

12. The method of claim 7, wherein the compound is formulated as a composition further comprising at least one pharmaceutically acceptable carrier.

13. The method of claim 7, wherein the subject is a mammal.

14. The method of claim 13, wherein the subject is human.

* * * * *